United States Patent [19]

Christensen et al.

[11] 4,060,687
[45] Nov. 29, 1977

[54] CEPHALOSPORINS HAVING A 3-α SUBSTITUTED ALKYL GROUPING

[75] Inventors: Burton G. Christensen, Metuchen; Ronald W. Ratcliffe, Matawan, both of N.J.

[73] Assignee: Merck & Co., Inc., Rahway, N.J.

[21] Appl. No.: 625,280

[22] Filed: Oct. 23, 1975

Related U.S. Application Data

[60] Division of Ser. No. 392,159, Aug. 27, 1973, Pat. No. 3,947,413, which is a continuation-in-part of Ser. No. 314,485, Dec. 12, 1972, abandoned, and Ser. No. 306,064, Nov. 13, 1972, abandoned.

[51] Int. Cl.$^2$ .................. C07D 501/16; A61K 31/545
[52] U.S. Cl. ........................................ 544/27; 544/16; 544/21; 544/26; 544/28; 544/24; 544/25; 544/29; 544/30; 544/54; 542/408; 542/420; 260/302R; 260/302 E; 424/246
[58] Field of Search ........... 260/243 C, 240 A, 240 K

[56] References Cited

U.S. PATENT DOCUMENTS

| | | | |
|---|---|---|---|
| 3,231,571 | 1/1966 | Eardley et al. | 260/243 C |
| 3,516,997 | 6/1970 | Takano et al. | 260/243 C |
| 3,819,623 | 6/1974 | Takano et al. | 260/243 C |

FOREIGN PATENT DOCUMENTS

| | | |
|---|---|---|
| 2,018,600 | 11/1970 | Germany. |
| 2,337,085 | 2/1974 | Germany. |
| 71-02255 | 1/1971 | Japan. |
| 71-24400 | 7/1971 | Japan. |
| 71-24713 | 7/1971 | Japan. |
| 71-24711 | 7/1971 | Japan. |

*Primary Examiner*—Nicholas S. Rizzo
*Assistant Examiner*—Diana G. Rivers
*Attorney, Agent, or Firm*—James A. Arno; Julian S. Levitt

[57] ABSTRACT

Novel cephalosporin compounds having a 3'-α-methyl, a 3-aryl or 3-heterocycle substituent are prepared by total synthesis. The novel cephalosporin compounds are active against gram-negative and gram-positive microorganisms.

3 Claims, No Drawings

CEPHALOSPORINS HAVING A 3-α SUBSTITUTED ALKYL GROUPING

This is a division of application Ser. No. 392,159 filed Aug. 27, 1973, now U.S. Pat. No. 3,947,413, which application is a continuation-in-part of U.S. application Ser. No. 314,485, filed Dec. 12, 1972 and U.S. application Ser. No. 306,064, filed Nov. 13, 1972, each abandoned.

The cephalosporins are valuable antibiotic substances useful in the treatment of pathogenic infections in humans and animals in addition to possessing utility for a variety of industrial applications. These products can be prepared from cephalosporins such as cephalosporin C and α-methoxy-7β-(D-5-carboxy-5-aminovaleramido)-3-carbamoyloxymethyl-3-cephem-4-carboxylic acid which are recovered from fermentation broths produced by growing suitable strains of micro-organisms. For example, cephalothin can be prepared from cephalosporin C by replacing the aminoadipoyl side chain with a 2-thienylacetyl group. However, processes for the preparation of cephalosporins suffer from several disadvantages. In the first place, the yields of cephalosporins obtained by fermentation are low, and the replacement of the aminoadipoyl group involves a number of steps which are difficult to carry out on a commerical scale. Other processes for preparing cephalosporins starting with the penicillin nucleus and synthetic methods are also known in the art. However, these processes likewise are difficult to carry out on a commercial scale and result in obtaining only low yields of the desired products. Accordingly, other methods suitable for the preparation of cephalosporin compounds on a large scale have been sought by many workers in this art.

It is an object of this invention to provide a new method for the total synthesis of cephalosporins. Another object is to provide novel compounds which are useful as intermediates for the preparation of novel cephalosporin compounds.

The invention further relates to novel cephalosporin compounds which possess antibiotic properties. These new cephalosporin compounds and particularly the salts and labile esters thereof are valuable new antibiotic substances which are effective against various gram-negative and gram-positive pathogens.

The new 3-cephem compounds of this invention can be represented by the structural formula

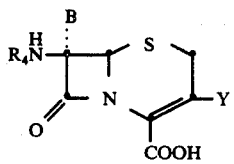

XI wherein
  Y represents t, —CHR$_5$ or R';
  R' represents aromatic, a heterocyclic group, or a substituted aromatic or heterocyclic group;
  R$_5$ represents a C$_1$-C$_3$ straight or branched chain alkyl group.

The substituent A can be hydrogen, hydroxy, halo, mercapto, acyloxy, acylthio, substituted hydroxy, substituted mercapto, a quaternary ammonium group, azido, cyano, amino or a N-substituted amino group. When A is hydroxy the cephem compound can also exist as the lactone which is formed by internal esterification with the carboxy group.

R$_4$ represents hydrogen or an acyl group, preferably a carboxylic acid acyl group.

B represents hydrogen, methyl, methoxy, or -SR wherein R is alkyl or aryl.

Included within the scope of the invention are nontoxic pharmaceutically salts and esters thereof conventionally employed in the penicillin and cephalosporin art.

The acyl radical represented by R$_4$ can be a substituted or unsubstituted aliphatic, aromatic or heterocyclic, araliphatic or heterocyclylaliphatic carboxylic acid radical or a carbothioic acid radical such as the acyl radicals of the known cephalosporins and penicillins. These acyl radicals can be represented by the general formula

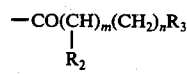

where R$_2$ is a radical of the group defined below, $m$ and $n$ represent 0–4 and R$_3$ represents R" or ZR", which are defined below.

One group of acyl radicals can be represented by the general formula

wherein R" represents a substituted or unsubstituted straight or branched chain alkyl, alkenyl, or alkynyl group; aryl, aralkyl; cycloalkyl; or a heteroaryl or heteroaralkyl group. These groups can be unsubstituted or can be substituted by radicals such as OH, SH, SR (R is alkyl or aryl), alkyl, alkoxy, halo, cyano, carboxy, sulfoamino, carbamoyl, sulfonyl, azido, amino, substituted amino, haloalkyl, carboxyalkyl, carbamoylalkyl, N-substituted carbamoylalkyl, guanidino, N-substituted guanidino, guanidinoalkyl, and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)-5-methyl-4-isoxazolyl, D-4-amino-4-carboxybutyl, D-4-N-benzoylamino-4-carboxy-n-butyl, p-amino-benzyl, O-aminobenzyl, m-aminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-quanidinophenyl)-4-isoxazolyl, 4-guanidinomethylphenyl, 4-guanidinomethylbenzyl, 4-quanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-napthylmethyl, 3-isothiazolylmethyl, 4-isothiazolylmethyl, 5-isothiazolylmethly, 4-pyridylmethyl, 5-isoxazolylmethyl, 4-methoxy-5-isoxazolylmethyl, 4-methyl-5-isoxazolymethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(5-methoxythienyl)methyl, 2- or 3-(4-chlorothienyl)-methyl, 2- or 3-(5-sulfothienyl)methyl, 2- or 3-(5-carboxythienyl)methyl, 3-(1,2,5-thiadiazolyl) methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, and tetrazolylmethyl.

The acyl group can also be a radical of the formula

wherein n is 0–4, Z represents oxygen or sulfur, and R" is defined as above. Representative members of the substituent

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pryidylthiomethyl, p-(carboxymethyl)phenoxymethyl, p-(carboxymethyl)-phenylthiomethyl, 2-thiazolylthiomethyl, p-(sulfo)phenoxymethyl, p-(carboxy)phenylthiomethyl, p-(carboxymethyl)phenoxymethyl, p-(carboxymethyl)-phenylthiomethyl, 2-pyrimidinylthiomethyl, phenethylthiomethyl, 1-(5,6,7,8-tetrahydronaphthyl)oxomethyl, 6,8-bis(methylthio)octanoyl.

Alternatively, the acyl group can be a radical of the formula

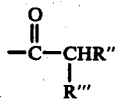

wherein R" is defined as above and R'" is a radical such as amino, hydroxy, azido, carbamoyl, guanidino, acyloxy, halo, sulfamino, tetrazolyl, sulfo, carboxy, carbalkoxy, and the like.

Also of interest is the following acyl moiety:

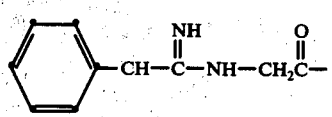

Representative members of the substituent

that might be mentioned are α-aminobenzyl, α-amino-2-thienyl, α-methylaminobenzyl, α-amino-methylmercaptopropyl, α-amino-3- or 4-chlorobenzyl, α-amino-3 or 4-hydroxybenzyl, α-amino-2,4-dichlorobenzyl, α-amino-3,4-dichlorobenzyl, β(−)-α-hydroxybenzyl, α-carboxybenzyl, α-amino-3-thienyl, α-amino-2-thienyl, D-(−)-α-amino-3-chloro-4-hydroxybenzyl, D(−)-α-amino-3-thienyl, 1-aminocyclohexyl, α-(5-tetrazolyl)-benzyl, 2-(α-carboxy)thienylmethyl, 3-(α-carboxy)-furylmethyl, α-sulfaminobenzyl, α-sulfamino-3-thienyl, α-(N-methylsulfamino)benzyl, D(−)-α-guanidino-2-thienyl, D(−)-α-guanidinobenzyl, α-guanylureidobenzyl, α-hydroxybenxyl, α-azidobenzyl, α-fluorobenzyl, 4-(5-methoxy-1,3-oxadiazolyl-aminomethyl, 4-(5-methoxy-1,3-oxadiazolyl)-hydroxymethyl, 4-(5-methoxy-1,3-oxadiazolyl)-carboxymethyl, 4-(5-methoxy-1,3-sulfadiazolyl)-aminomethyl, 4-(5-methoxy-1,3-sulfadiazolyl)-hydroxymethyl, 4-(5-methoxy-1,3-sulfadiazolyl)-carboxymethyl, 2-(5-chlorothienyl)-aminomethyl, 2-(5-chlorothienyl)-hydroxymethyl, 2-(5-chlorothienyl)-carboxymethyl, 3-(1,2-thiazolyl)-aminomethyl, 3-(1,2-thiazolyl)-hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfobenzyl, α-phosphonobenzyl, α-diethylphosophono, and α-monoethylphosphono.

Alternatively, the group

can be a sulfonamido group such as phenylsulfonamido, ethylsulfonamido, benzylsulfonamido, 2,5-dimethylsulfonamido, 4-chlorosulfonamido, 4-chlorophenylsulfonamido, 4-methoxysulfonamido, and the like.

The acyl substituents of the general formula

wherein $R_{10}$ and $R_{11}$ are as defined below represent a preferred group of substituents because of their generally useful antibiotic activity. $R_{10}$ represents hydrogen, halo, amino, guanidino, phosphono, hydroxy, tetrazolyl, carboxy, sulfo, or sulfamino. $R_{11}$ represents phenyl, substituted phenyl, a monocyclic heterocyclic 5- or 6-membered ring containing one or more oxygen, sulfur or nitrogen atoms in the ring, substituted heterocycles, phenylthio, heterocyclic or substituted heterocyclic thio groups; or cyano. The substituents can be halo, carboxymethyl, guanidino.

Pursuant to a preferred embodiment of this invention, $R_4$ is represented by the formula

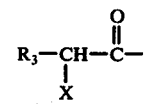

wherein X is hydrogen, halogen, amino, guanidino, phosphono, hydroxy, tetrazolyl, carboxy, sulfo, or sulfamino; $R_3$ is phenyl, substituted phenyl, a monocyclic heterocyclic 5- or 6-membered ring containing one or more oxygen, sulfur or nitrogen atoms in the ring, substituted heterocycles, phenylthio, phenyloxy, heterocyclic or substituted heterocyclic thio groups, lower alkyl (1–6 carbon atoms), or cyano; the substituents on the $R_3$ group being halo, carboxymethyl, guanidino, guanidinomethyl, carboxyamidomethyl, aminomethyl, nitro, methoxy or methyl. Particularly preferred are acyl groups where X is hydrogen, hydroxy, amino or carboxy and $R_3$ is phenyl, lower alkyl or a 5- or 6-membered heterocyclic ring having one or two sulfur, oxygen or nitrogen hetero atoms. Thus, specific $R_3$ substituents that might be mentioned as preferred substituents are tetrazolyl, thienyl, furyl and phenyl.

With respect to the term "A"; A can be a halo such as chloro, bromo or fluoro.

When A is substituted hydroxy or substituted mercapto group, it can be shown by the formula —$ZR_x$ where Z is oxygen or sulfur, and $R_x$ is an acyl group, a straight chain or branched chain loweralkyl (1–6C), alkenyl (1–6C) or alkynyl group (1 –6C); an aryl group; an aralkyl group; or a heterocyclic group such as heteroaryl or heteroalkyl. The heterocyclic group is preferable a 5- or 6-membered ring containing one or more sulfur, nitrogen or oxygen atoms. These groups can be unsubstituted or can be substituted by radicals such as alkyl (1–6 carbons), alkoxy (1–6 carbon atoms), halo, cyano, carboxy, carbamoyl, azido, sulfo, amino, substituted amino, haloalkyl, carboxyalkyl, carbamoylalkyl, N-substituted amino, haloalkyl, carboxyalkyl, carbamoylalkyl, N-substituted carbamoylalkyl, guanidino, N-substituted guanidino, guanidinoalkyl, sulfamyl, substituted sulfamyl, and the like.

Representative of the groups —$ZR_x$ thus presented that might be mentioned are isoxazolylthio, pyrolidenylthio, 1,3,4-thiadiazolylthio, 1-oxidopyridylthio, furazanylthio, tetrazolylthio, thienylthio, thiazolylthio, furylthio, pyranylthio, pyrrolylthio, imidazolythio, pyrazolylthio, pyridylthio, pyrazinylthio, pyrimidinylthio, pyridazinylthio, isothiazolylthio, methoxy, n-propoxy, methylthio, acetoxy, propionyloxy, benzoyloxy, (p-chlorobenzoyl)oxy, (p-methylbenzoyl)oxy, pivaloyloxy, (1-adamantyl)carboxy, butanoyloxy, carbamoyloxy, (N-methylcarbamoyl)oxy, (N-ethylcarbamoyl)-oxy, [N-(2-chloroethyl)carbamoyl]oxy, (N-phenylcarbamoyl)oxy, (N-p-sulfophenylcarbamoyl)oxy, p-carboxymethylphenylcarbamoyloxy, methoxycarbonyloxy, isobutanoyloxy, cyclobutylcarbonyloxy, carbamoylthio, (ethoxythiocarbonyl)thio, (N-propoxythiocarbonyl)thio, (cyclopentanoxythiocarbonyl)thio, methylthio, N,N-diethylthiocarbamoylthio, N-methylpiperazinium-1-thiocarbonylthio, N,N-dimethylpiperazinium-1-thiocarbonylthio, 2-furoylthio, isothiouronium, (5-methyl-1,3,4-thiadiazol-2yl)thio, p-tolysulfonylthio, mesyloxy, 1-mesyloxy, 1-methyl-1,2,3,4-tetrazolyl-5-thio, tosyloxy, sulfamoyloxy, 1-naphthoyloxy, 2-furylacetoxy, cinnamoyloxy, p-hydroxycinnamoyloxy, p-sulfocinnamoyloxy and 1R:2S-epoxypropylphosphonyloxy.

Alternatively, when A is hydroxy, the cephalosporin can also exist as the lactone which is formed by internal esterification with the carboxy group.

The substituent A can also be a group of the general formula

—$Y_1$ wherein $Y_1$ represents amino or substituted amino including nitrogen heterocycles and substituted heterocyclic groups. Examples of such groups that might be mentioned are amino, acetamido, carbamoylamino, N,N-dimethylamino, N-(2-chloroethyl)amino, 5-cyanotriazol-1-yl, 4-methoxycarbonyltriazol-1-yl.

When A is amino the cephalosporin compound can also exist as the lactam formed by loss of water with the adjacent carboxy group.

Representative of the quaternary ammonium groups representing A that might be mentioned are pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-(carboxymethyl)pyridinium, 4-(hydroxymethyl)pyridinium, 4-(trifluoromethyl)pyridinium, quinolinium, picolinium and lutidinium.

The preferred groups representing A are hydrogen, halo, azido, cyano, hydroxy, alkoxy, aryloxy, aralkyloxy, heterocycleoxy, mercapto, alkylthio, arylthio, aralkylthio, heterocyclethio, amino, alkylamino, alkanoylamino, hydroxyphenyl, acylthio, acyloxy, isothiouronium, sulfamoyloxy, quaternary ammonium, a heterocyclic tertiary amine, alkylsulfonyloxy and (cis-1,2-epoxypropyl)phosphono. The heterocycles can be a 5 or 6-membered hetero ring containing one or more nitrogen, oxygen or sulfur atoms. The acyl group can be a loweralkanoyl group of 2–6 carbon atoms, carbamoyl, or thiocarbamoyl and N-alkyl or N,N-dialkyl derivatives thereof. The alkyl group of the foregoing substituents contains 1–6 carbon atoms and may be further substituted by radicals such as alkoxy, halo, amino, cyano, carboxy, sulfo, and the like.

The novel 3-cephem compounds of the invention may be prepared by the processes shown in the following flowsheet:

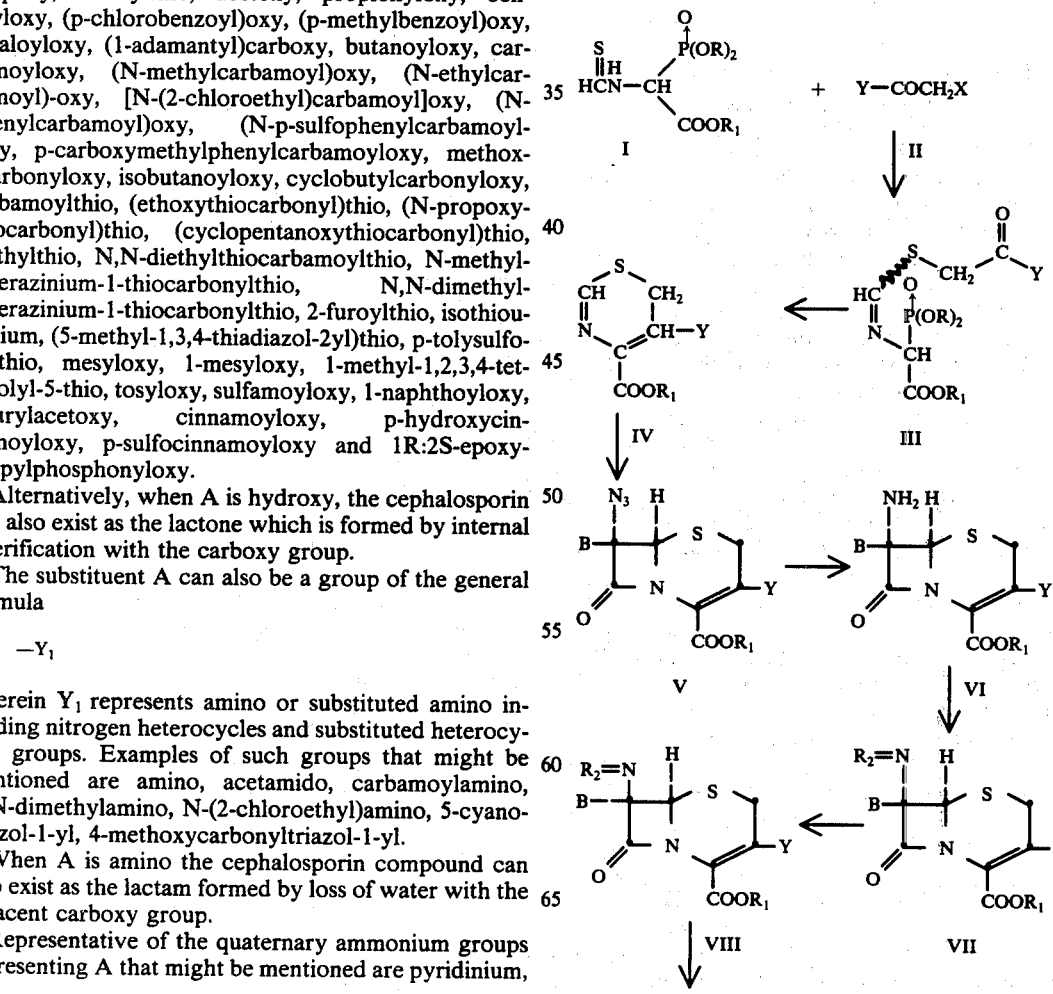

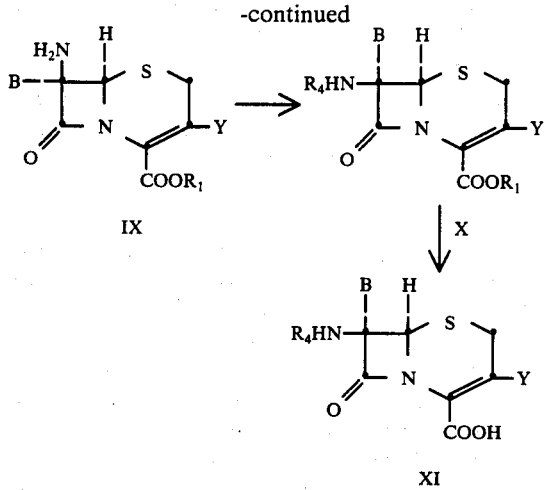

The starting material in this process is an α-thioformamido phosphonoacetate ester shown in formula I. Various esters of the starting material shown in formula I above can be utilized as starting materials in the above-shown process. Thus, various phosphono esters, for example the dilower alkyl esters, or the diaryl esters, are suitable for use in this process. Representative of the esters that may be employed include those wherein R may be the same or different, and is, for example, methyl, ethyl, propyl, butyl, pentyl, phenyl, benzyl and the like.

The carboxy group of phosphono starting material may be blocked or protected, preferably by the use of a group ($R_1$) which can be ultimately removed to obtain the free acid form of the cephalosporin without disruption of the α-lactam moiety. Protecting groups suitable for this purpose are indeed well known in this art. Examples of suitable protecting ester groups that might be mentioned are those of alcohols, phenols, and the like. $R_1$ is preferably an alkyl or aralkyl group containing from 1 to about 20 carbon atoms. Thus, $R_1$ can be a lower alkyl group such as methyl, ethyl or tertiary butyl, a substituted alkyl such as phthalimidomethyl, succinimidomethyl, phenacyl, substituted phenacyl such as p-bromophenacyl, a β-substituted ethyl group such as 2,2,2-trichlorethyl, 2-methylthioethyl or 2-(p-methylphenyl)-ethyl, an alkenyl group such as 3-buten-1-yl, propenyl, allyl, etc., an alkoxyalkyl group such as methoxymethyl, an aryloxyalkyl such as p-methoxyphenoxymethyl, an aralkyloxyalkyl group such as benzyloxymethyl, benzyl or a substituted benzyl group such as p-nitrobenzyl, p-methoxybenzyl, 3,5-dinitrobenzyl, 2,4,6-trimethylbenzyl or 3,5-dichloro-4-hydroxybenzyl, benzhydryl or a substituted benzhydryl group such as p-methoxybenzhydryl, and the like. Preferred blocking groups are methyl, tertiary butyl, phenacyl, p-bromophenacyl, p-nitrobenzyl, 2,2,2-trichloroethyl, p-methoxybenzyl, benzhydryl, methoxymethyl and p-methoxyphenoxymethyl.

Examples of representative starting materials (I) that might be mentioned are trichloroethyl α-thioformamidodiethylphosphonoacetate, trichloroethyl α-thioformamidodiphenylphosphonoacetate, phenyl α-thioformamido-dimethylphosphonoacetate, p-methoxybenzyl α-thioformamido-diethylphosphonoacetate, benzhydryl α-thioformamido-diphenylphosphonoacetate, t-butyl α-thioformamido-dimethylphosphonoacetate, t-butyl α-thioformamido-dipropylphosphonoacetate, methyl α-thioformamido-diphenylphosphonoacetate, phenacyl or p-bromophenacyl α-thioformamido-diethylphosphonoacetate, methoxymethyl α-thioformamido-dimethylphosphonoacetate, p-methoxyphenoxymethyl α-thioformamido-dimethylphosphonoacetate, and p-nitrobenzyl α-thioformamido-dimethylphosphonoacetate.

The first step of the process shown above is carried out by reacting the thioformamido ester (I) with a substituted acetone of the formula II wherein X represents a leaving group such as a sulfonate, for example p-toluene sulfonate, methyl sulfonate, a benzoate group, for example p-nitrobenzoate, a halogen, particularly chlorine or bromine; or trifluoromethylsulfonyloxy.

Y represents phenyl, a heterocyclic group, or a substituted phenyl or heterocyclic group. The heterocyclic group is preferably a 5- or 6-membered ring containing one or more sulfur, nitrogen or oxygen atoms such as furyl, thienyl, thiazolyl, thiadiazolyl, pyridyl, pyrazolyl, tetrazolyl and the like. The substituents on the phenyl or heterocyclic group can be lower alkyl ($C_1$ - $C_6$), lower alkoxy ($C_1$-$C_6$), halo, cyano, carbolower alkoxy, acylamino, dialkylamino, and the like. Y further represents $$R_5-\overset{A}{\underset{}{C}H}-$$

wherein $R_5$ is a $C_1$-$C_3$ straight or branched chain alkyl group; and A is as defined above. The reaction may be carried out at temperatures varying from 0° C. to 50° C. in the presence of an acid scavenger to produce the corresponding S-substituted thioformimidate compound (III). Thus, the reaction is conveniently carried out by reacting the intermediate product I with the substituted acetone II in the presence of about one equivalent of an inorganic base such as an alkali metal carbonate, for example, potassium carbonate or nonnucleophilic organic bases such as diazobicyclononane and bis-1,8-(dimethylamino)naphthlene, and di-isopropylethylamine at room temperature. After the reaction is complete, the product is conveniently isolated by filtering the reaction mixture and evaporating the filtrate to dryness.

Representative examples of substituted acetones that may be employed in the practice of the invention include 1-chloro-3-acetoxy-butan-2-one, 1-bromo-3-propionyloxy-butan-2-one, 1-bromo-3-butryloxy-butan-2-one, 1-chloro-3-propionyloxy-hexane-2-one, 1-bromo-3-acetoxy-butan-2-one, 1-chloro-3-propionyloxy-butan-2-one, 1-chloro-3-butyryloxy-butan-2-one, 1-chloro-3-acetoxypentan-2-one, 1-bromo-3-propionyloxy-hexan-2-one and the like. Further illustrative of the members that may be employed are phenacyl chloride, p-chlorophenacyl chloride, p-cyanophenacyl chloride, p-carbomethoxyphenacyl chloride, 4-chloroacetylpyridine, 2-chloroacetylfuran and 2-chloroacetyl-5-methylfuran, 2-chloroacetyl-thiophene, 2-bromoacetylthiazole, 2-chloroacetylthiadiazole, 4-bromoacetyl-pyrazole, 5-bromotetrazole and the like.

The intermediate S-substituted thioformimidate compound (III) upon reaction with a base such as an alkali metal carbonate or hydride or an organo lithium compound such as phenyllithium is converted to the corresponding thiazine compound (IV). Alternatively, the thiazine may be produced by the condensation of the thioformamido derivative (I) and the substituted acetone (II) in the presence of more than about one equivalent of the base. Thus, the thiazine is produced almost exclusively when two or more equivalents of potassium carbonate are used in the condensation reaction.

The intermediate thiazine compound IV or the mixture of this product with the acetonyl compound III is then reacted with an azidoacetyl reagent in the presence of an acid scavenger and preferably in a solvent medium at temperatures varying from −78° C. to 30° C. to afford the 7-azido compound (V).

The azidoacetyl reactants of particular interest have the following formula:

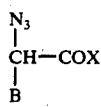

wherein B is hydrogen, methyl, methylthio or methoxy and X is halogen, $OSO_2CF_3$ or $OSO_2CH_3$. The reaction is preferably carried out at low temperatures, for example at about 0° C., and in the presence of a sufficient amount of base such as a tertiary amine which serves as an acid scavenger and, in addition, catalyzes the cyclization of the intermediate thiazine compound. Thus, the reaction is conveniently carried out adding a solution of the azide in methylene chloride to a cool solution of the thiazine and a tertiary amine such as triethylamine in the same solvent; the amine being present in molar equivalent amount. The reaction mixture is stirred in the cold until the formation of the desired 7-azido cephalosporin compound is complete. Azidoacetyl halide and 2-azido-2-methylacetyl halide are well known and may be prepared in accordance with procedures taught in the art. The preparation of 2-azido-2-methoxyacetyl halide and the azido acetyl sulfonates are described below.

Examples of representative thiazine compounds (IV) that might be mentioned are

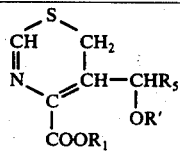

| $R_1$ | R' | $R_5$ |
|---|---|---|
| methoxymethyl | $CH_3$—CO | $CH_3$ |
| " | $CH_3$—CO | $C_2H_5$ |
| " | $C_2H_5$—CO | $CH_3$ |
| " | $CH_3CO$ | $C_3H_7$ |
| P-methoxybenzyl | $C_3H_7$—CO | $CH_3$ |
| " | $C_2H_5$—CO | $C_3H_7$ |
| " | $C_2H_5$—CO | $C_2H_5$ |
| " | $C_4H_9$—CO | $CH_3$ |
| " | $C_3H_7$—CO | $C_2H_5$ |
| p-nitrobenzyl | $C_4H_9$—CO | $C_3H_7$ |
| " | $C_4H_9$—CO | $C_2H_5$ |
| " | $C_5H_{11}$—CO | $CH_3$ |
| " | $C_5H_{11}$—CO | $C_2H_5$ |

Further illustrative of the thiazines that may be employed are the following: p-methoxybenzyl-5-phenyl-6(H)-1,3-thiazine-4-carboxylate, p-methoxybenzyl-5-p-chlorophenyl-6(H)-1,3-thiazine-4-carboxylate, p-methoxybenzyl-5-p-cyanophenyl-6(H)-1,3-thiazine-4-carboxylate, p-methoxybenzyl-5-p-carbomethoxyphenyl-6(H)-1,3-thiazine-4-carboxylate, p-methoxybenzyl-5-(4-pyridyl)-6(H)1,3-thiazine-4-carboxylate, p-methoxybenzyl-5-(2-furyl)-6(H)-1,3-thiazine-4-carboxylate and p-methoxybenzyl-5(5-methyl-2-furyl)-6(H)-1,3-thiazine-4-carboxylate.

Alternatively, the desired 7-azido compound (V) is obtained by reacting a mixture of the acylic compound (III) and the cyclic thiazine compound (IV) or the acyclic compound (III) per se with the azido-acetyl reagent under the described conditions. When the acyclic compound (III) per se is reacted with the azido-acetyl halide it is postulated that a cyclic intermediate compound of the structure

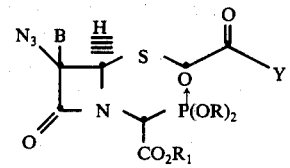

is formed, and that this product is then cyclized under the reaction conditions to the desired 7-azido compound (V).

In the reactions I-IV above, the phosphonate group is used as an activating group and is finally cleaved in the preparation of the thiazine intermediate. Other starting compounds having activating groups such as methyl sulfinyl and dimethylsulfonium can be similarly used in the described reactions.

In the next step of this reaction sequence the 7α-azido compound (V) is reduced to obtain the corresponding 7α-amino compound (VI). For example, this reduction is conveniently effected with hydrogen in the presence of a noble metal catalyst such as platinum oxide in accordance with methods known in this art. Other reductive methods that may be employed include $H_2S$-$Et_3N$, $NH_4HS$, NaHS, Al/Hg-THF, or Cu/phenylmercaptan. The carboxy blocking group is readily removed to afford the 7α-amino-3-Y-3-cephem-4-carboxylic acids in accordance with processes known in this art. For example, the benzhydryl, tertiary butyl, p-methoxybenzyl and p-methoxyphenoxymethyl groups are cleaved with an acid such as trifluoroacetic acid and the 2,2,2-trichloroethyl and phenacyl groups are cleaved by reaction with zinc and acetic acid.

It should be noted that when B = Me, OMe or SR (compound V), a mixture of 7α and 7β isomers are obtained of which the 7β is the major isomer. Accordingly the 7β compound may be reduced directly to the 7β-amino (compound IX) using procedures well known in the art and as described herein.

The 7β-azido and 7β-aminocephalosporin compounds produced by the above-described process are obtained as mixtures of the d and l enantiomers which can be resolved in accordance with methods known in this art to obtain the optically-active forms. The dl 7α-amino compounds, or the enantiomers thereof, can be converted to the corresponding 7β-aminocephalosporin compounds and these β-substituted compounds can be acylated to produce cephalosporins having valuable antibiotic properties.

The epimerization process for the conversion of the 7α-amino-3-cephem compounds to the corresponding 7β-amino-3-cephem are described and claimed in the copending application of Raymond A. Firestone Ser. No. 306066 filed 11-13-72.

The epimerization process proceeds as follows: (B = H)

The 7α-amino cephalosporin (VI) is reacted with an aromatic aldehyde to form an imino adduct (VII) wherein $R_2$ represents an aromatic substituent. The aromatic aldehyde is preferably benzaldehyde or a substituted benzaldehyde having in the ortho or para position a substituent such as nitro, methyl, halo, sulfonyl, carboxyl, derivatives such as esters or amides, cyano and the like. The preferred aromatic aldehydes are benzaldehyde, p-nitrobenzaldehyde, p-chlorobenzaldehyde, and salicylaldehyde.

Other carbonyl containing compounds, e.g., aldehydes and ketones such as acetone, hexafluoroacetone or chloral which will form stable imino derivatives will also be operable in this invention. Also, polycyclic aromatic aldehydes can be used, i.e., having 2-3 fused ring nuclei.

The 7α-amino cephalosphorin (VI) and the aromatic aldehyde are mixed together in approximately equimolar amounts in an inert solvent. Suitable solvents are ethanol, dioxane, acetonitrile, dimethylformamide, dimethylsulfoxide, benzene, toluene, methylene chloride, chloroform, and the like. The reaction proceeds readily at temperatures ranging from ambient to reflux temperature of the solvent. Since this condensation is an equilibrium reaction and since water is one of the products of the reaction, water is removed from active participation in further reactions by any of a number of usual methods, including azeotropic distillation, molecular sieves, chemical entrapment using potassium carbonate, magnesium sulfate, etc., or borate esters. The particular method is dependent upon the exact parameters of the reaction. The reaction is terminated by evaporation of the solvent. The 7α-imino derivative II is then recovered and used in the next step.

The 7α-imino derivative VII is then dissolved in an inert aprotic solvent. A particularly suitable solvent is tetrahydrofuran. Then an equivalent or more of a strong base is added. The strong base functions as an "activating agent" and can be either organic or inorganic. Most suitable are lithium alkyls and lithium aryls, such as lithium alkyls having 1-4 carbon atoms, e.g., t-butyl lithium, n-butyl lithium, or phenyl lithium. Sodium hydride is also suitable as is lithium diisopropylamide.

The activating agent is added to the solution of compound VII at a low temperature (−11° to 0° C. and preferably −100° to −60° C.), preferably under an inert atmosphere. The amount of activating agent employed is from 1-23 equivalent weights.

Following addition of the strong base (phenyl lithium is particularly preferred), a co-solvent, which is a dipolar aprotic solvent, is added to the mixture. By the term "dipolar aprotic solvent" I mean a strongly dipolar solvent having no acidic protons. Suitable solvents are many, and this usage is well known in the art. Preferred solvents include dimethylformamide, dimethylsulfoxide, hexamethylphosphoramide, N-methyl pyrrolidone, or dimethylacetamide.

The solvent and the co-solvent are preferably employed sequentially, as described, although this is not critical; the solvent, co-solvent, and strong base can operably be added in any order to the 7α-imino compound.

Following the addition of the solvent, base, and co-solvent to the 7α-imino compound, a molecular excess) from 1-5 equivalents) of an acid is added in one addition as quickly as possible. The acid employed can be any organic or inorganic acid; the only limitation is that it not affect the cephalosporin ring. Preferably, a lower carboxylic acid is employed having 1-5 carbon atoms; most preferably, acetic acid is used when a carboxylic acid is used; it can be added as a tetrahydrofuran solution or in the presence of water. The acid serves as a source of protons which exist as solvated protons in the reaction solution.

After the acid has been added, the compound VIII, the 7β-imino compound, is present in the reaction mixture. This can be isolated using standard purification techniques.

The 7β-imino compound VIII can then be regenerated to the 7β-amino compound IX. This process utilizes the reaction of VIII with an amine in the presence of an acid catalyst. The amine employed can be aniline, hydrazine, or hydrazine derivatives such as phenylhydrazine, 2,4-dinitrophenylhydrazine, and the like. The acid catalyst can be any commonly used strong organic or inorganic acid such as hydrochloric acid or p-toluene sulfonic acid. One preferable combination utilizes aniline hydrochloride, which serves as both acid and amine. Another preferred combination is 2,4-dinitrophenyl hydrazine and p-toluene sulfonic acid. The reaction conditions of the regeneration are chosen such that no undesired hydrolysis or ring damage occurs, and is preferably carried out in a lower alkanol medium (1-5 carbon atoms), such as methanol, ethanol, and the like, although other solvents including dimethoxyethane tetrahydrofuran or dimethylformamide may also be used. The temperature is that of the surroundings. The relative amounts of acid and amine employed depends on the specific aldehyde and amine used, since the regeneration involves an equilibrium. The choice of amounts of the reagents is within the skill of one in the art.

The above reaction conditions are suitable for removal of difficult hydrolyzable Schiff's bases, such as those with strong electronegative groups. When the Schiff's base was formed, e.g., with benzaldehyde, the following methods can also be used to regenerate the amine.

The 7β-imino compound can be dissolved in ether, and then added slowly to an ether solution of p-toluene sulfonic acid. No additional amine is needed. The formed salt will either crystallize or oil out of solution. Following removal of the ether by decanting or the like, the tosylate salt is treated wth aqueous pH 8 solution and extracted to recover the desired 7β-amino compound.

An alternate route involves treatment of the 7β-imino compound with pH 2-2.5 buffer for 5-15 minutes, extracting with ether to remove the free aldehyde, then neutralizing to pH 8 and extracting to recover the 7β-amino compound.

All the compounds described in the above Flow Sheet, since they result from a total synthesis procedure, are racemic mixtures of both d- and l-forms. The separation of the two optically active components can be conveniently done at the end of the synthesis indicated, i.e., when the compound of Formula IX is obtained. Alternatively, the compound of Formula IX can be acylated to yield d,l-7β-acylamino cephalosporins, and then separated using readily available processes. For example, resolution can be accomplished by reaction with an optically active base, separation of the resulting diastereomers, and reconversion of the diastereomers to the free acid or a salt thereof.

The dl-7β-aminocephalosporin compounds (IX) prepared as described above are acylated to obtain new dl cephalosporin compounds of the formula X and deblocked resulting in the corresponding free acid (XI).

In accordance with a further embodiment of the invention, when B is hydrogen, dl-7α-azido compound (XII) is reduced to obtain the corresponding novel dl-7α-amino compound (XIII) as follows:

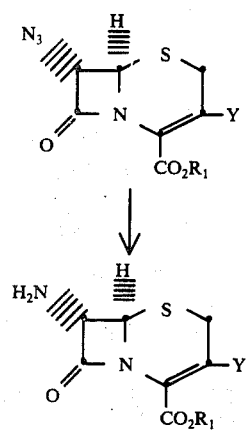

For example, reduction to the amino is conveniently effected with hydrogen in the presence of a noble metal catalyst such as platinum oxide, aluminum amalgam, zinc and acetic acid or copper and thiophenol in accordance with methods known in this art. The carboxy blocking group may be readily removed to afford the 7α-amino-3-Y-3-cephem-4-carboxylic acids in accordance with processes known in this art. For example, the benzhydryl, tertiary butyl, p-methoxybenzyl and p-methoxyphenoxymethyl groups are cleaved with an acid such as trifluoroacetic acid and the 2,2,2-trichloroethyl and phenacyl groups are cleaved by reaction with zinc and acetic acid. The term "blocking group" as utilized herein is employed in the same manner and in accordance with the teaching of U.S. Pat. No. 3,697,515; the contents therein with respect to said blocking group being incorporated herein by reference.

The novel 7α-azido and 7α-aminocephalosporin compounds obtained therefrom (wherein B is hydrogen) are obtained as mixtures of the d and l enantiomers which can be resolved in accordance with methods known in this art to obtain the optically-active forms. The novel dl 7α-amino compounds or the enantiomers thereof can be converted to the corresponding novel dl 7β-aminocephalosporin compounds by procedures hereinafter described and these 7β-substituted compounds can be acylated to produce novel dl cephalosporins having valuable antibiotic properties. Alternatively, as is hereinafter shown, the dl 7α-azido compounds can be converted to obtain antibiotically active 7-substituted, for example 7-methoxy, or 7-methyl, cephalosporins.

A method by which the dl 7-a-azido compounds can be converted to obtain antibiotically active 7-methoxy, 7-SR or 7-methyl cephalosporins is as follows:

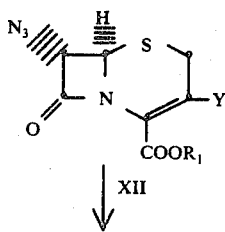

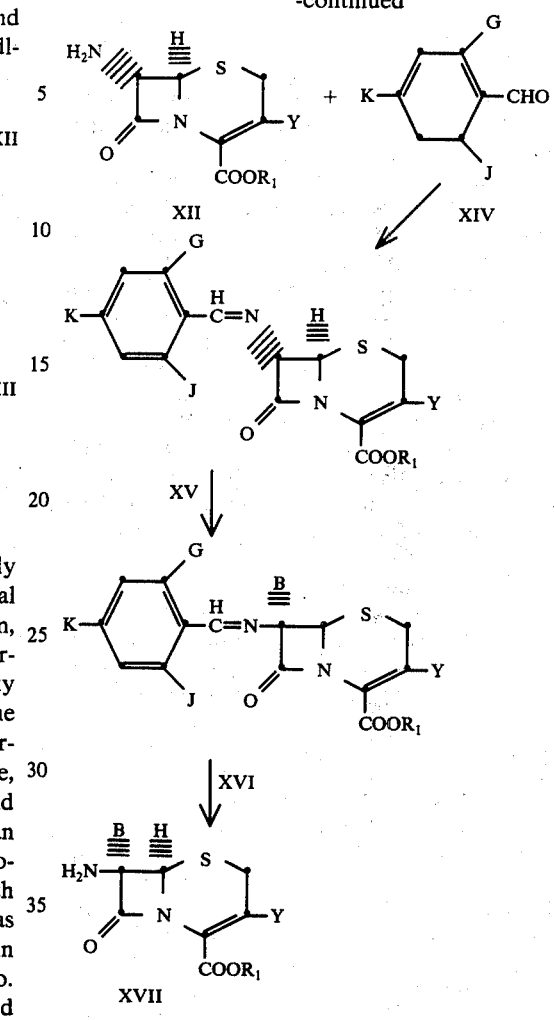

A convenient and well-known procedure for resolution of the dl-cephalosporin compounds includes reaction with an optically active base, separation of the resulting diastereomers, and reconversion of the diastereomers to the free acid or a salt thereof.

The process can be summarized briefly as having three major steps: the first is the preparation of the imino derivative of then 7-amino cephalosporin. This imino derivative is the substituted with the chosen reactant supplying the B group desired (CH₃, —SR or OCH₃). The specific reactant depends on the identity of the B group. The third step is then the regeneration of the amino group.

The dl 7-α-azido starting material is reduced via methods known to the art to the dl 7-α-amino cephalosporin. The reactant XIV employed in the reaction with the 7α-amino is an aromatic aldehyde, optionally having at least one o- or p-electronegative substituent. In other words, at least one of J, G, and K may be a substituent selected from the group consisting of nitro, halo, sulfonyl, carboxyl derivatives such as esters or amides, cyano, and the like. The other two of J, G, and K can either be one of the above electronegative substituents, or hydrogen. The preferred reactants are p-nitrobenzaldehyde, where K-nitro, and G and J-hydrogen, and benzaldehyde.

Other carbonyl containing compounds, e.g., aldehydes and ketones such as acetone, hexafluoroacetone or chloral which will form stable imino derivatives will also be operable in this invention. Also, polycyclic aromatic aldehydes can be used, i.e., having 2-3 fused ring nuclei.

The dl 7α-amino cephalosporin XIII and the aromatic aldehyde XIV are mixed together in approximately equimolar amounts in an inert solvent. Suitable solvents are ethanol, dioxane, acetonitrile, dimethylformamide, tetrahydrofuran, dimethylsulfoxide, benzene, toluene, methylene chloride, chloroform, and the like. The reaction proceeds readily at temperatures ranging from ambient to reflux temperature of the solvent. Since this condensation is an equilibrium reaction and since water is one of the products of the reaction, water is removed from active participation in further reactions by any of a number of usual methods, including azeotropic distillation, molecular sieves, chemical entrapment using potassium carbonate, magnesium sulfate, etc., or borate esters. The particular method is dependent upon the exact parameters of the reaction. The reaction is terminated by evaporation of the solvent. The imino derivative XV is then recovered and used in the next step.

The latter involves the substitution of the B group at the carbon atom adjacent to the imino nitrogen. This reaction takes place in the presence of an inert solvent, such as those listed above, and in the additional presence of an activating agent which is an organic or inorganic base.

The activating agent can be any of a number of organic or inorganic bases. Tertiary (loweralkyl) amines are suitable, such as triethylamine, diisopropyl ethylamine; lower alkyl is used as having 1-4 carbon atoms and can be the same or different. Pyridine is also used. Lithium alkyls and lithium aryls, such as lithium alkyls having 1-4 carbon atoms, e.g., t-butyl lithium or phenyl lithium, could be used. Sodium hydride, lithium amides such as lithium diisopropylamide, and potassium t-butoxide are also suitable.

The activating agent is added to the solution of compound XV at a low temperature (−100 to 0° C. and preferably −100 to −60° C.) and under an inert atmosphere.

The activated compound XV is not isolated, but the next reagent is added directly to the reaction mixture.

The specific reagent which is employed in the reaction with the activated compound XV to result in the substitution of the chosen B group obviously depends on the B group desired.

In the case of B = OCH₃ the reagent can be dimethyl peroxide, methyl t-butyl peroxide, methylphenylsulfenate, o-methyldimethyl sulfoxonium methosulfate, or N-methoxy pyridinium methosulfate. It may be noted that an alternative method for the introduction of the OCH₃ group involves reaction of activated XV with a halogenating agent such as N-bromosuccinimide followed by methanolysis. Where B = CH₃ the following reagents may be employed: methyl sulfate, methyl chloride, methyl bromide and methyl iodide.

Once the compounds XVI have been prepared, the imino moiety is converted to the amino moiety of compound XVII.

The regeneration of XVII from XVI takes place by the reaction of XVI with an amine in the presence of an acid catalyst. The amine employed can be aniline, hydrazine, or hydrazine derivatives such as phenylhydrazine, 2,4-dinitrophenyl hydrazine, and the like. The acid catalyst can be any commonly used strong organic or inorganic acid such as hydrochloric acid or p-toluene sulfonic acid. One preferable combination utilizes aniline hydrochloride, which serves as both acid and amine. Another preferred combination is 2,4-dinitrophenyl hydrazine and p-toluene sulfonic acid. The reaction conditions of the regeneration are chosen such that no undesired hydrolysis or ring damage occurs, and is preferably carried out in a lower alkanol medium (1-5 carbon atoms), such as methanol, ethanol, and the like, although other solvents including dimethoxyethane or dimethyl formamide may also be used. The temperature is that of the surroundings. The relative amounts of acid and amine employed depends on the specific aldehyde XIV and amine used, since the regeneration involves an equilibrium. The choice of amounts of the reagents is within the skill of one in the art. XVI can be hydrolyzed with PdCl₂ in the presence of H₂O.

Compounds XV and XVI prepared in the reactions can be used to prepare valuable antibacterial agents useful against gram-positive and gram-negative bacteria. When the amino group of compound XVII is acylated as illustrated on the next page the resulting products have activity against gram-negative organisms.

An alternative procedure by which the novel dl-7-azido compounds may be converted to useful antibiotically active 7-methoxy cephalosporins is as follows:

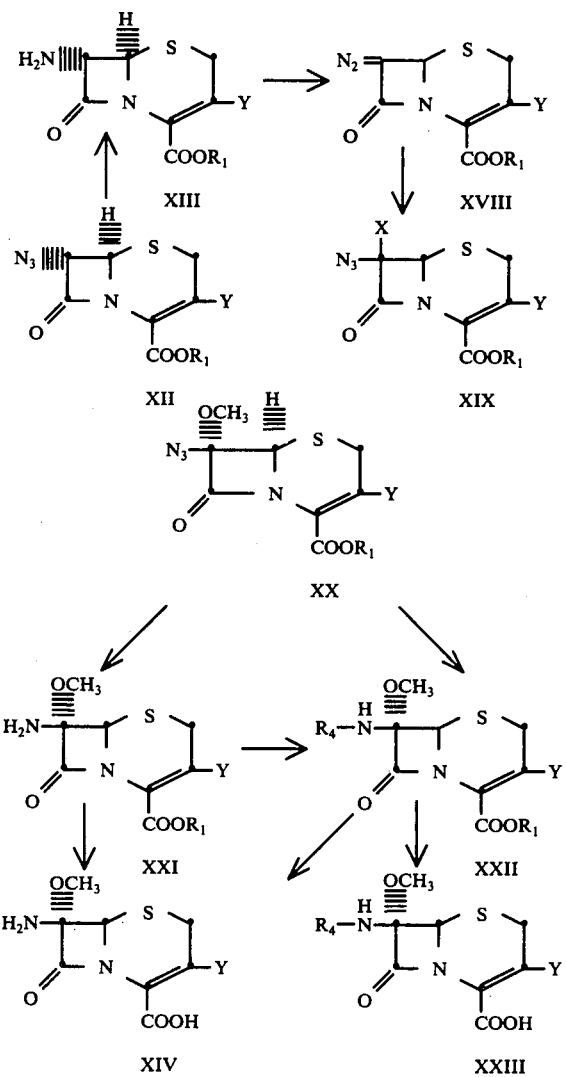

where the substituents are as defined above.

In the above process the novel dl 7-azido compound XII is reduced to the 7-amino cephalosporin XIII. The 7-amino compound is converted to the corresponding 7-diazocephalosporin acid ester by reaction with nitrite. It should be noted that although the 7α-amino compound is illustrated in the above flowsheet, it will be appreciated that the 7β-cephalosporin formed by epimerization of the 7α-amino compound can also be employed in the above sequence of reactions leading to antibiotically active 7-methoxy cephalosporins. The 7-diazocephalosporanic acid ester XVIII is then reacted with a halo azide from the group consisting of bromine, chlorine or iodine azide, preferably in the presence of a tertiary amine azide, to produce the intermediate 7-halo-7-azidocephalosporanic acid ester XIX which on reaction with a suitable nucleophilic reagent is converted to the desired 7—OCH$_3$-7—azidocephalosporanic acid ester XX. This intermediate product is reduced and acylated in one step to form the substituted cephalosporanic ester XXII which can then be cleaved to remove the blocking group and obtain the cephalosporanic acid or a salt thereof XXIII. Alternatively, as shown in the flowsheet, the 7—OCH$_3$—7—azidocephalosporanic acid ester XX is reduced to the 7—OCH$_3$—7—aminocephalosporanic acid ester XXI which can be acylated to produce the 7—OCH$_3$—7—acylaminocephalosporanic acid ester XXII. Alternatively, the ester group of compound XXI can be cleaved to obtain the free acid XIV which can be acylated to form the desired substituted cephalosporin or a salt thereof. The step of cleaving the blocking group is readily effected in accordance with methods known in this art. For example, an aralkyl group such as the benzyl ester is removed by reduction, a silyl ester can be removed by hydrolysis to form the free acid or a salt thereof and a benzhydryl group is readily cleaved by reaction with trifluroacetic acid in the presence of anisole. In this process other esters which are readily cleaved to form the free acid such as trichloroethyl, phthalimidomethyl, succinimidomethyl, p-methoxybenzyl, p-nitrobenzyl, phenacyl and t-butyl and the like can be used. Also, as is discussed above, the 3-substituent on the Δ$^3$- cepham nucleus can be varied following the procedures known in this art to obtain the useful cephalosporins.

The diazotization of the 7-amino ester is carried out in accordance with processes well known in this art. Thus, it is conveniently effected in aqueous or aqueous-organic solvent medium, for example by reaction with sodium nitrite in the presence of an acid or by reaction with an organic nitrite. Organic solvents suitable for carrying out this reaction are those which do not contain an active hydrogen. Examples of such solvents that might be mentioned are methylene chloride, ether, benzene, toluene, chloroform, and the like. The reaction is preferably carried out at temperatures between about 0° and 50° C.; usually it is most conveniently effected at room temperature. The isolation of the desired diazo compound is readily accomplished in accordance with methods known in the art.

The step of producing the halo azide intermediate is carried out by reacting the diazo compound with a halo azide at a temperature between about −25° and 50° C. for sufficient time to complete the formation of the desired compound. The reaction is preferably carried out in a suitable organic solvent medium which is inert to the reactants. Various solvents which do not contain an active hydrogen such as methylene chloride, chloroform, benzene, toluene, ether and the like, or mixtures thereof provide suitable mediums for carrying out the reaction. Generally, it is preferred to effect the reaction in the presence of a second azide such as lithium azide or a tertiary ammonium azide, for example triethylammonium azide, since under these conditions the formation of the undesired 7-dibromo compound is avoided. The halo azide is used in an amount in slight excess of stoichemetric requirements. The amount of second azide is not critical and it is generally desirable to use an excess in order to obtain maximum yields of the desired halo azido compound under optimum conditions. After completion of the formation of the halo azide the product is recovered and can be purified further, for example by chromatography, in accordance with processes well known in this art.

The next step of the process comprising the replacement of the halo substituent by a methoxyl group is effected by reacting the halo azide with a substance capable of furnishing an OCH$_3$ group to replace the halo. This reaction is preferably carried out in the presence of a suitable non-reactant solvent such as methylene chloride, chloroform, benzene, toluene, ether, petroleum ether and the like; again it is desirable to avoid using any solvents containing an active hydrogen. Thus, the nucleophilic displacement reagent can be methanol which results in the displacement of the halo group and the introduction of a methoxy group. The reaction is preferably carried out in the presence of a heavy metal cation such as a silver salt.

In the next step of the above-described process the 7—azido—7—OCH$_3$ compound is then reduced to afford the corresponding 7—amino—7—OCH$_3$ compound. Various methods of carrying out this reduction can be employed, but it is generally preferred to carry out the reduction of the azido to the amino group by catalytic hydrogenation employing a noble metal catalyst such as platinum, palladium or oxides thereof. These processes are carried out in accordance with procedures well known in this art. Alternatively, the reduction can be effected in the presence of a suitable acylating agent to produce the desired 7-acylamido—7—OCH$_3$ compound. The 7-amino compound can be reacted with suitable acylating agents using procedures well known in this art as described hereinafter to obtain the desired 7-acylamido compounds.

In accordance with a further embodiment of this invention the novel dl 7β-aminocephalosporin compounds of the invention may be acylated to obtain the corresponding novel dl 7β-acylamido cephalosporin compounds which are active against pathogenic gram-negative and gram-positive bacteria. Acylation of the novel dl 7α-amino cephalosporins results in the preparation of novel dl 7α-acylamido compounds which may be converted by known methods to novel antibiotically active dl-7β-acylamido cephalosporins. The novel dl 7-acylamido cephalosporins may be resolved into the respective d- and l-isomer utilizing resolution techniques well known to the art. As indicated above, the novel dl 7α-azido or dl 7α-amino cephalosporin compounds may be resolved to produce the corresponding d- or l- isomer which may be converted to known useful cephalosporins employing techniques well known in the art.

The novel dl 7α- or 7β-cephalosporins of the invention have the following formula:

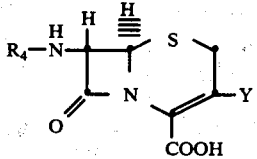

and salts and esters thereof wherein Y is as defined above; and $R_4$ is an acyl group, for example an acyl group such as those of useful penicillins and cephalosporins known in this art. Pursuant to a preferred embodiment $R_4$ is represented by the formula

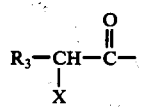

where X is hydrogen, halogen, amino, guanidine, phosphono, hydroxy, tetrazolyl, carboxy, sulfo, or sulfamino; $R_3$ is hydrogen, phenyl, substituted phenyl, an N-substituted acetimidoyl amino such as N-(phenylacetimidoyl)amino, a monocyclic heterocyclic 5- or 6-membered ring containing one or more oxygen, sulfur or nitrogen atoms in the ring, substituted heterocycles, phenylthio, phenyloxy, heterocyclic or substituted heterocyclic thio groups, lower alkyl (1–6 carbon atoms), or cyano; the substituents on the $R_3$ group being halo, carboxymethyl, guanidino, guanidinomethyl carboxamidomethyl, aminomethyl, nitro, methoxy or methyl. Particularly preferred are acyl groups where X is hydrogen, hydroxy, amino or carboxy and $R_3$ is phenyl, lower alkyl or a 5- or 6-membered heterocyclic ring having one to four sulfur, oxygen or nitrogen hetero atoms. Thus, specific $R_3$ substituents that might be mentioned as preferred substituents are thiazolyl, thienyl, furyl, N-(phenylacetimidoyl)amino and phenyl.

In accordance with this invention, it is now found that novel dl 7β-azido-7-methyl (or 7-methoxy or 7-SR) cephalosporin compounds are prepared by reacting a 5-substituted-6H-1,3-thiazine-4-carboxylic acid ester with a 2-azido-2-methoxyacetyl halide or a 2-azido-2-methylacetyl halide as shown in the following equation:

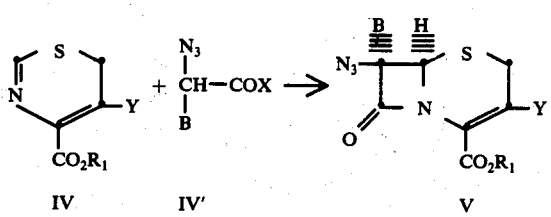

wherein $R_1$, Y and X are as set forth above and B is $-CH_3$, $-SR$ or $-OCH_3$.

Pursuant to a further embodiment of our invention, the novel dl-7β-azido-7-methoxy and dl-7β-azido-7-methyl cephalosporin compounds of this invention are reduced, for example by hydrogenation in the presence of a catalyst, preferably a noble metal catalyst such as platinum oxide, to produce the corresponding dl-7β-amino-7-methoxy and dl-7β-amino-7-methyl cephalosporin compounds. The racemic 7β-azido compounds of this invention can be resolved to obtain the individual isomers in accordance with methods known in the art for the resolution of racemates. Alternatively, the dl-cephalosporin compounds obtained by acylation of the dl-7β-amino compounds obtained by acylation of the dl-7β-amino compounds can be resolved.

The novel dl-7β-azido-7-methoxycephalosporin and dl-7β-azido-7-methyl (or 7-SR) cephalosporin compounds of the present invention can be converted to novel racemic 7β-acylamido-7-methoxy or 7-methyl cephalosporin compounds. This involves reducing the azide to the corresponding 7β-amino compound and acylating this intermediate product to obtain the corresponding novel dl 7β-acylamido-7-methoxycephalosporin ester or 7β-acylamido-7-methyl (or 7-SR) cephalosporin ester which is then deblocked to obtain the free acid and salts thereof. Thus, the new racemic compounds of this invention can be used to prepare racemic cephalosporins such as 7-methyl-7β-(2-thienylacetamido)3-Y-cephem-4-carboxylic acid, and 7-methoxy-7β-(2-thienylacetamido)-3-Y-cephem-4-carboxylic acid and their salts. These products are antibiotics which are active against various gram-negative and gram-positive pathogens. These racemates can also be resolved by procedures known in the art to obtain the individual isomers.

Thus, in accordance with a further embodiment of this invention, the novel dl-7β-aminocephalosporin compounds can be acylated to obtain new dl cephalosporin compounds of the formula:

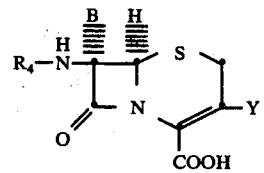

and salts and esters thereof wherein Y is as defined above, B is $-CH_3$, $-SR$ or $-OCH_3$, and $R_4$ is an acyl group as defined above, such as those of penicillins and cephalosporins known in this art. The above dl-cephalosporin compounds are active against gram-negative and grampositive bacteria. It should be noted that the racemates of the invention which have approximately one-half the activity of the particular isomer of interest may be resolved to obtain the active enantiomer in accordance with techniques well known to the art.

Thus, the novel dl cephalosporins of this invention are prepared by the acylation of the corresponding substituted novel dl 7-aminocephalosporanic acid compounds. This embodiment of the present invention can be illustrated by the following reactions:

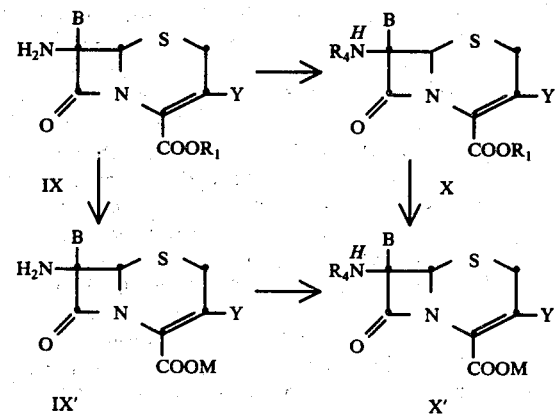

wherein B is H, $-SR$, $OCH_3$ or $CH_3$, M represents hydrogen, a metal cation or an amine, Y and $R_4$ are the same as defined above and $R_1$ represents a blocking group. In accordance with the foregoing flowsheet, the dl 7α- or 7β-aminocephalosporanate IX is acylated to form the corresponding cephalosporin derivative X which is deblocked to form the desired cephalosporin X' or a salt thereof. Alternatively, the amino-cephalosporin can first be deblocked to produce the corresponding acid or a salt thereof IX' and this intermediate can then be acylated to obtain the desired cephalosporin or a salt thereof.

The acylation of the 7-amino-cephalosporanic acid compound is readily effected by reaction with an acylating agent such as an acyl halide (chloride or bromide) or a functional equivalent thereof such as an acid anhydride, a mixed acid anhydride with other carboxylic acids and particularly lower aliphatic esters of carboxylic acid, a carboxylic acid in the presence of a carbodiimide such as 1,3-dicyclohexylcarbodiimide, an activated ester and the like, or enzymatic acylation pursuant to acylation methods used for the preparation of cephalosporins which are well known in this art.

As discussed above, the 7-substituted-7-aminocephalosporanic acid compound acylated can be a suitably blocked ester, such as the benzhydryl, p-methoxybenzyl, trichloroethyl, trimethylsilyl, phenacyl or methoxymethyl ester which is removed in accordance with the procedures known in the art to produce the desired cephalosporin or a salt thereof. Thus for example, when the blocking group is benzhydryl, it can be readily removed by reaction with trifluoroacetic acid in the presence of anisole. Alternatively, the 7-amino-cephalosporanic acid ester can first be converted to the free acid by this procedure and the salt of the free acid by this procedure and the salt of the free acid such as the sodium salt or an amine salt can be acylated pursuant to procedures well known in the art which are used for the conversion of 6-amino-penicillanic acid and 7-aminocephalosporanic acid to produce various penicillins and cephalosporins.

It may be noted that the substituent at the 3-position of the cephalosporin nucleus may be converted to or readily replaced by other Y substituents pursuant to methods well known in this art. For example, upon treating the 3-acetoxyethyl substituted cephalosporanates of this invention with a suitable reagent or combination of reagents, it is possible to substitute various substituents for acetoxy at the 3-position of the cephalosporin nucleus. Suitable reagents include, for example, phosgene and a secondary amine, isocyanates, alkali metal toluenesulfinates, alkali metal azide, polyhydroxybenzene, N-loweralkyl indole, thiourea, mercaptans, phosphorus pentachloride, thiocyanates, heterocyclic thiols, cycloalkyl xanthates, pyridine, thiobenzoic acid, N-alkyl and N,N-dialkylthioureas or alkali metal N-alkyl and N,N-dialkylthiocarbamates and the like.

Thus by reaction with a heterocyclic thiol, for example 1-methyl-1,2,3,4-tetrazole-5-thiol or 5-methyl-1,3,4-thiadiazole-2-thiol, the 3-acetoxy cephalosporin is converted to the corresponding heterothioethyl compound.

Also, by reaction with a quaternary ammonium compound, for example pyridine, the 3-acetoxy cephalosporin is converted to the corresponding 3-pyridinoethyl compound. Alternatively, the 3-acetoxy cephalosporins upon treatment with citrus acetylesterase are converted to the corresponding 3-hydroxyethyl compounds which can be acylated to produce other 3-acyloxyethyl including carbamoyloxyethyl, or acylthioethyl compounds. Similarly, other 3-substituted cephalosporin compounds are prepared following procedures well known in this art.

One method for the introduction of an N,N-diloweralkylcarbamoyloxyethyl or heterocyclic aminocarbonyloxyethyl moiety at position 3 of the instant products consists in treating a 3-hydroxyethyl analog such as a 3-hydroxyethyl-7-methoxy-7-(2-thienylacetamido)cephalosporanic acid with phosgene and a diloweralkylamine in the presence of a base. In this manner the following products can be obtained: sodium dl-3-(N,N-dimethylcarbamoyloxyethyl)-7-methoxy-7-(2-thienylacetamido)decephalosporanate and sodium dl-3-(pyrrolidinylcarbonyloxyethyl)-7-methoxy-7-(2-thienylacetamido)decephalosporanate.

The N-mono substituted carbamoyloxyethylcephalosporin products are obtained by treating a 3-hydroxyethyl-7-amidodecephalosporanate with a suitable isocyanate. In this manner sodium dl-3-(N-methylcarbamoyloxyethyl)-7-methoxy-7-(2-thienylacetamido)-decephalosporanate with methylisocyanate in the presence of sodium bicarbonate.

The unsubstituted carbamoyloxyethyl may be obtained by cleaving an N mono- or di-substituted carbamoyloxyethyl material such as N,N-di-p-methoxybenzylcarbamoyloxyethyl or N-2,2,2-trichloroethyl carbamoyloxyethyl. An alternative method for obtaining the carbamoyloxyethyl group at the 3-position involves treating the 3-hydroxyethyl analog with trichloroacetylisocyanate or chlorosulfonylisocyanate, followed by hydrolysis.

Thus the new cephalosporins of the formula

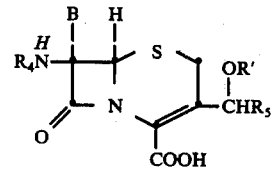

and the esters and salts thereof wherein $R_4$ represents an acyl group and B, R' and $R_5$ are as defined above, prepared as described above, are converted to the corresponding compounds having a 3-substituent of the formula

wherein A' represents a substituent other than lower alkanoyloxy using procedures known in the cephalosporin art for replacing the acetoxy group with other substituents. Thus, the acetoxy group of such compounds can be cleaved to produce the corresponding 3-(1-hydroxy)-alkyl compound by enzymatic hydrolysis with acetylesterase. The resulting hydroxy group may be then reacted to form other substituents at the 3-position. For example, the 3-hydroxy group may be reesterified with a lower alkanoic acid group or with an aryl acid group by employing acylating agents such as a lower alkyl or aryl carboxylic acid halide or anhydride, and substituted carbamoyl halide or a lower alkyl isocyanate.

The 3-acetoxy group may also be converted to other analogs by replacing the acetoxy group of I with nitrogen or sulfur nucleophiles. Many nitrogen and sulfur nucleophiles are well known in the cephalosporin art and the following examples are merely illustrative of the type of compound which may be employed; for example, a tertiary amine such as pyridine and the like, a 5-membered heterocyclic thiol such as 5-methyl-1,3,4-thiadiazolyl- 2-thiol, N-methyl-tetrazolylthiol and the like. Alternatively, the 3-acetoxy group can be cleaved by catalytic hydrogenation to afford the 3-($C_2$-$C_4$) alkyl compounds.

Thus, by the foregoing processes, the following new 3-cephem compounds are obtained: 3-(1-carbamoyloxyethyl)-7-(2-thienylacetamido)-3-cephem-4-carboxylic acid, 3-(1-pyridiniumethyl)-7-(2-furylacetamido)-3-cephem-4-carboxylic acid, 3-[1-(5-methyl-1,3,4-thiadiazol-2-yl)-ethyl]-7-(1-tetrazolylacetamido)-3-cephem-4-carboxylic acid, 3-(1-propyl)-7-(D-phenylglycylamido)-3-cephem-4-carboxylic acid, and the like.

It should be noted that when B is hydrogen, the reaction involving the azido-acetyl reagent results in the production of a 7-α-azido cephalosporin whereas when B is $CH_3$,SR,$OCH_3$, the reaction of the azidomethoxyacetyl halide or azidomethylacetyl halide produces a 7-β-azido compound.

As indicated above, the acyclic precursor of the thiazine, or a mixture of the acyclic and thiazine compounds, may be used to produce the 7-azido cephalosporin. However, it is generally preferred to react the azidoacetyl reagent with the thiazine since maximum yields of the desired cephalosporin compounds are obtained under such conditions.

In the above described series of reactions the phosphonate group is used as an activating group and is finally cleaved in the preparation of the thiazine intermediate. Other starting compounds having activating groups such as

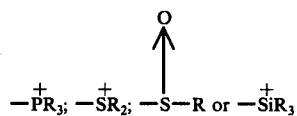

wherein R is lower alkyl (preferably methyl) or aryl (e.g., phenyl, etc.) may be employed as the starting material (I) in reaction with a thionoformate ester and ultimately cleaved in the preparation of the thiazine intermediate.

The α-aminophosphonoacetate ester (I) used as the starting material in the process described above is obtained by the processes shown in the following flowsheet:

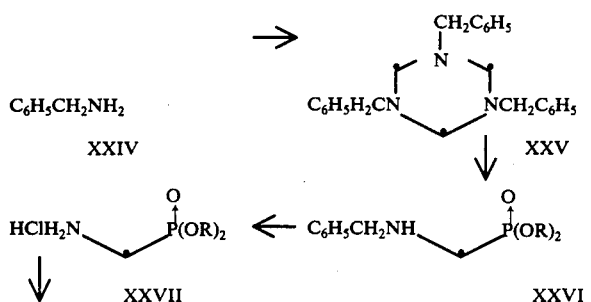

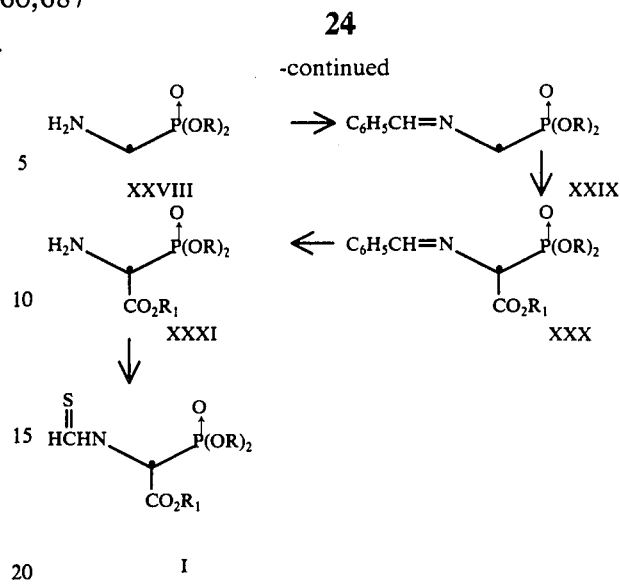

wherein R and $R_1$ are as defined above. In accordance with the above-depicted reactions, benzylamine is first reacted with formaldehyde to obtain the 1,3,5-tribenzyl-sym-hexahydrotriazine XXV. The latter compound on reaction with a di-substituted phosphite is converted to the phosphonate XXVI. This reaction is conveniently effected by heating a mixture of the di-substituted phosphite with the triazine at 100° C. for sufficient time to complete the formation of the desired intermediate product which is conveniently isolated as an acid salt, such as the hydrochloride. Reduction of the intermediate N-benzylaminomethylphosphonate acid salt in the presence of palladium on carbon affords the salt of the corresponding amino compound XXVII. The acid salt is converted to the amine by reacting it with ammonia in a suitable solvent medium such as chloroform. After removing the precipitated ammonium salt, the desired product is readily recovered by evaporating the solvent to obtain the aminomethylphosphonate ester XXVIII. Alternatively, the acid salt XXVII is neutralized with aqueous $K_2HPO_4$ and the free amine XXVIII is extracted into an organic solvent such as $CH_2Cl_2$. This latter product on reaction with an aldehyde such as benzaldehyde is converted to the corresponding Schiff base XXIX, which on reaction with a strong base e.g. an organolithium compound such as phenyllithium and then a haloformate ester is converted to the imine XXX. Treatment of this imine with 2,4-dinitrophenyl hydrazine in the presence of p-toluenesulfonic acid monohydrate or with p-toluenesulfonic acid hydrate in ether followed by neutralization of the amine acid salt affords the desired α-aminophosphonoacetate ester XXXI which is converted to α-thioformamido-phosphonoacetate ester (I) employing

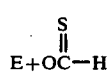

in $CCl_4$.

Representative of the novel cephalosporins that may be prepared in accordance with the processes of the invention are the following:

| | R₄ | R₅ | A | B |
|---|---|---|---|---|
| | ![phenylglycyl] PhCH(NH₂)C(O)- | —CH₃ | —OC(O)NH₂ | H |
| | ![thienylacetyl] 2-thienyl-CH₂C(O)- | —CH₃ | pyridinium (N⊕) | H |
| | ![furylacetyl] 2-furyl-CH₂C(O)- | —CH₃ | —OC(O)NH₂ | H |
| | ![p-hydroxyphenylglycyl] HO-C₆H₄-CH(NH₂)C(O)- | —CH₃ | —OC(O)NH₂ | H |
| | HO-C₆H₄-CH(NH₂)C(O)- | —CH₃ | H | H |
| | ![thiazolylacetyl] thiazol-4-yl-CH₂C(O)- | —CH₃ | —OCH₃ | CH₃ |
| | ![phenyl-CH(CH₃)-like] PhCH(CH₃)C(O)- (α-methylphenylacetyl) | —CH₃ | —O-C(O)CH₃ | OCH₃ |
| | ![tetrazolylacetyl] 1H-tetrazol-1-yl-CH₂C(O)- | —CH₃ | —OC(O)CH₃ | OCH₃ |
| | 3-thienyl-CH₂C(O)- | —CH₃ | —OC(O)NH₂ | H |
| | PhCH(COOH)C(O)- | —CH₃ | —OC(O)NH₂ | H |
| | 2-thienyl-CH(COOH)C(O)- | —CH₃ | —OC(O)NH₂ | H |
| | PhCH₂C(O)- | —CH₃ | —OC(O)NH₂ | H |
| | 3-Br-C₆H₄-CH₂C(O)- | —CH₃ | H | CH₃ |

-continued
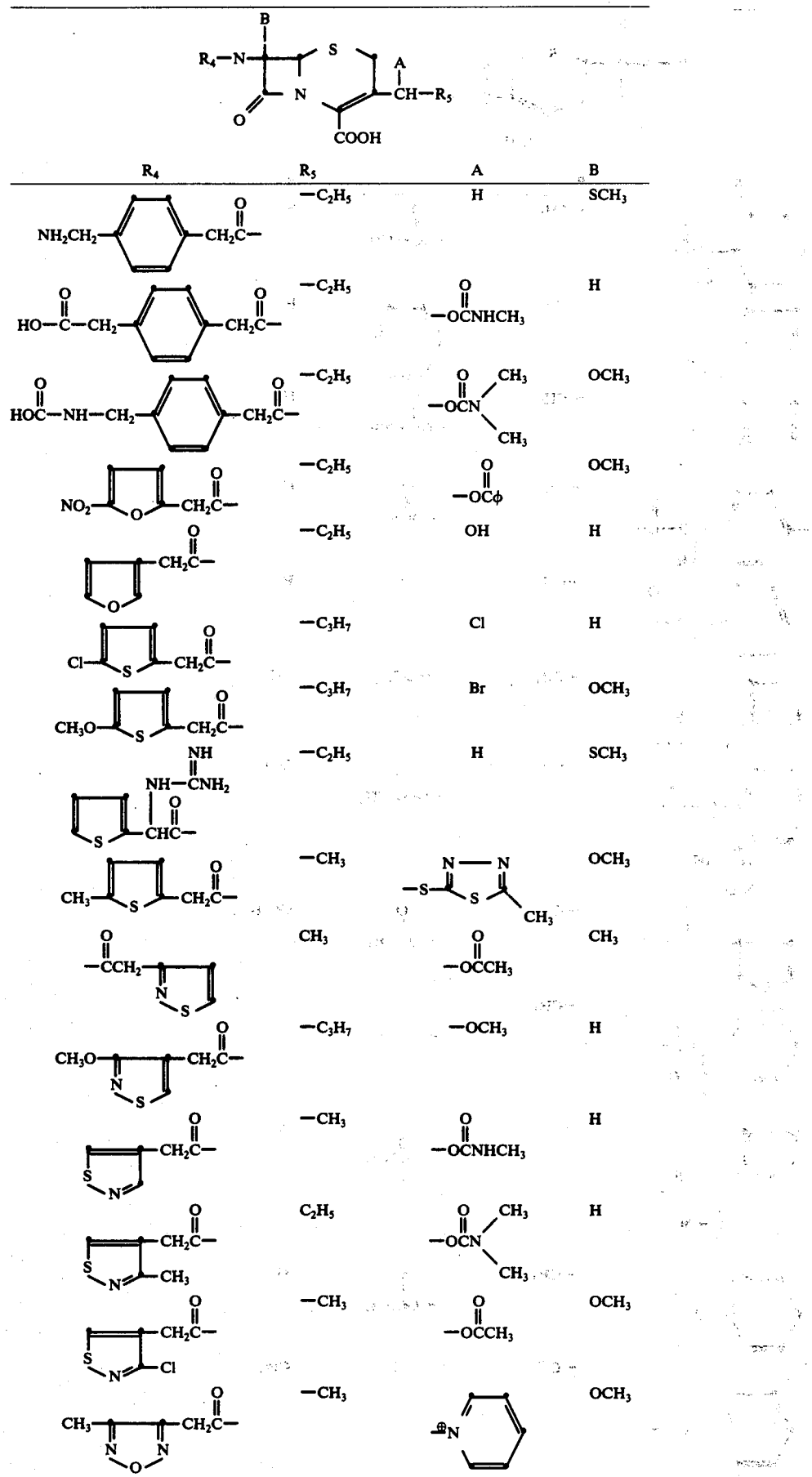

-continued

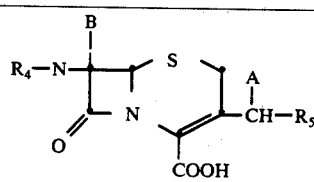

| R₄ | R₅ | A | B |
|---|---|---|---|
| (1,2,5-thiadiazol-3-yl)-CH₂-C(=O)- | —C₂H₅ | Cl | OCH₃ |
| (4-methyl-1,2,5-thiadiazol-3-yl)-CH₂-C(=O)- | —C₂H₅ | pyridinium | OCH₃ |
| (4-chloro-1,2,5-thiadiazol-3-yl)-CH₂-C(=O)- | —CH₃ | -S-(5-methyl-1,3,4-thiadiazol-2-yl) | OCH₃ |
| (thien-2-yl)-CH₂-C(=O)- | CH₃ | OCOCH₃ | H |
| (thien-2-yl)-CH₂-C(=O)- | CH₃ | OC(=O)NH₂ | OCH₃ |
| (thien-2-yl)-CH₂-C(=O)- | CH₃ | OC(=O)NH₂ | H |
| Ph-CH(NH₂)-C(=O)- | CH₃ | H | H |
| Ph-CH(OH)-C(=O)- | CH₃ | -S-(1-methyltetrazol-5-yl) | H |
| Ph-CH(OH)-C(=O)- | OCH₃ | -S-(1-methyltetrazol-5-yl) | H |
| (1,2,3-triazol-1-yl)-CH₂-C(=O)- | CH₃ | -S-(5-methyl-1,3,4-thiadiazol-2-yl) | H |

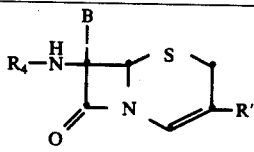

| R₄ | R' | B |
|---|---|---|
| (3-methoxy-1,2,4-thiadiazol-5-yl)-CH₂-C(=O)- | phenyl | H |
| Ph-S-CH₂-C(=O)- | 4-Cl-phenyl | H |

-continued

| R₄ | R' | B |
|---|---|---|
| (pyridin-3-yl)-S-CH₂-C(=O)- | 2-CN-phenyl | H |
| CN-CH₂-C(=O)- | thiazol-2-yl | H |

-continued

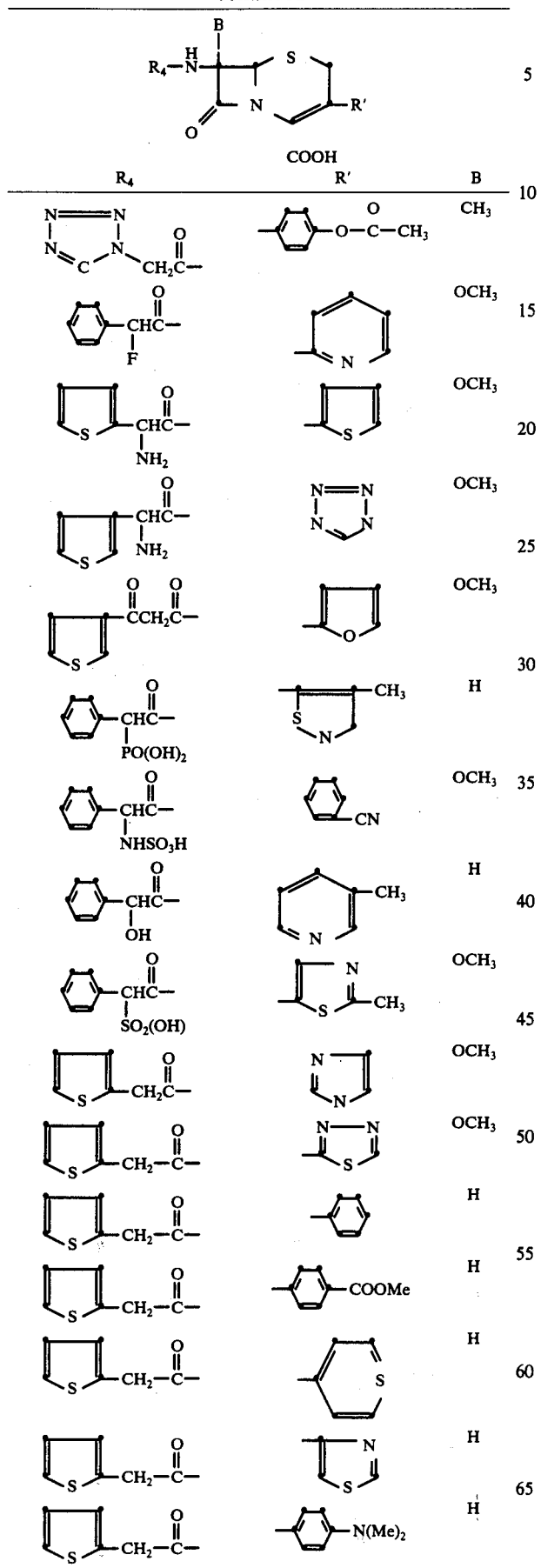

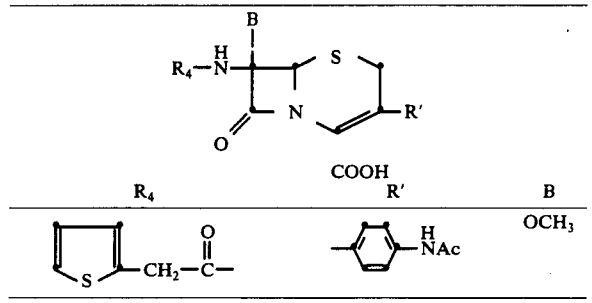

EXAMPLE 1 p-Methoxybenzyl α-[S-(α-acetoxy)-propionylmethylthioimidato]-diethylphosphonoacetate A mixture of 77 mg. p-methoxybenzyl α-thioformamido diethylphosphonoacetate, 35 mg. of 1-chloro-3-acetoxy-butan-2-one, 29 mg. powdered potassium carbonate and 2 ml. acetone is stirred 18 hours at room temperature under nitrogen. The mixture is filtered and evaporated, affording 92% yield of crude p-methoxybenzyl α-[S-(α-acetoxy)-propionylmethylthioimidato]-diethylphosphonoacetate.

The 1-chloro-3-acetoxy-butan-2-one used as the starting material in this example is prepared as follows:

A solution of 2-acetoxy-propionoyl chloride (10.0 g.) in anhydrous ether is added dropwise over 45 min. to an ice-cold, stirring solution of diazomethane (2.82 g.) and triethylamine (6.7 g.) in anhydrous ether. The mixture is stirred an additional 3 hours in the cold, then filtered through a pad of magnesium sulfate. The etheral filtrate of crude diazoketone is cooled in an ice bath, and a stream of anhydrous hydrochloric acid is bubbled through the solution for 10 min. The resulting mixture is washed with ice-cold water and ice-cold 5% aqueous sodium bicarbonate, dried over magnesium sulfate, filtered and evaporated under reduced pressure. Distillation of the residue affords 1-chloro-3-acetoxy-butan-2-one in 52% yield.

This product has the following physical properties: B.P. 43°–44° C./0.18 mm. Mass Spectrum M+ at m/e 164 IR (neat) 5.65, 5.75, 8.02, 9.1, 9.6, 10.5, 11.45, 12.8μ NMR (CDCl$_3$) τ 8.5 (d, 3, J=8 Hz, CHC$\underline{H}_3$), 7.7 (s, 3, C$\underline{H}_3$CO), 5.89 (s, 2, ClC$\underline{H}_2$CO), 4.6 (q, 1, J=8 Hz, C$\underline{H}$CH$_3$)

EXAMPLE 2 p-Methoxybenzyl 5-(1-acetoxyethyl)-6(H)-1,3-thiazine-4-carboxylate p-Methoxybenzyl α-[S-(α-acetoxy)-propionylmethylthioimidato]-diethylphosphonoacetate, prepared as described in Example 1, is flushed 3 times with tetrahydrofuran, evaporated, dissolved in 1 ml. of 1,2-dimethoxyethane, and treated with 5 mg. of oil-free sodium hydride suspended in 1 ml. of 1,2-dimethoxyethane. After stirring 5 minutes, benzene is added and the solution is washed with water, dried with magnesium sulfate, filtered and evaporated to afford p-methoxybenzyl 5-(1-acetoxyethyl)-6(H)-1,3-thiazine-4-carboxylate. The product so obtained has the following physical properties: Mass Spectrum M+ −60 at m/e 289 NMR (CDCl$_3$) τ 8.5 (d, 3, J=8 Hz, CHC$\underline{H}_3$), 8.0 (s, 3, C$\underline{H}_3$CO), 6.85 (m, 2, SC$\underline{H}_2$), 6.2 (s, 3, OC$\underline{H}_3$), 4.85 (s, 2, C$\underline{H}_2$Ar), 3.85

(q, 1, J=8 Hz, C$\underline{\text{H}}$CH$_3$), 2.95 (ABq, 4, Ar$\underline{\text{H}}$), 1.6 (s, 1, N=CH). IR (CHCl$_3$) 3.45, 5.78, 5.82, 6.21, 6.31, 6.62, 6.90, 7.30, 7.69, 8.2, 8.5, 8.85, 9.12, 9.45, 9.65, 9.85, 10.5, 12.05μ.

EXAMPLE 3 p-Methoxybenzyl 5-(1-acetoxyethyl)-6(H)-1,3-thiazine-4-carboxylate

A mixture of p-methoxybenzyl α-thioformamido-diethylphosphonoacetate (1.73 g.), powdered potassium carbonate (1.83 g.), 1-chloro-3-acetoxy-butan-2-one (0.82 g.), and acetone (30 ml.) is stirred for 5 hours under a nitrogen atmosphere. The reaction mixture is filtered and the filtrate evaporated under reduced pressure. The residue is dissolved in carbon tetrachloride, washed with pH 9 phosphate buffer and water, dried over magnesium sulfate, filtered, and evaporated in vacuo to yield crude p-methoxybenzyl 5-(1-acetoxyethyl)-6(H)-1,3-thiazine-4-carboxylate in 92% yield. The product so obtained has the following physical properties: IR (CHCl$_3$) 5.74, 5.84, 6.2, 6.3, 6.65, 6.9, 7.3, 7.69, 8.0, 8.5, 9.12, 9.95, 10.5, 12.05μ.

EXAMPLE 4 p-Methoxybenzyl dl-3-(1-acetoxyethyl)-7α-azido-3-cephem-4-carboxylate p-Methoxybenzyl 5-(1-acetoxyethyl)-6(H)-1,3-thiazine-4-carboxylate, prepared as described in Example 2 from 462 mg. (1.23 mmole) of p-methoxybenzyl α-thioformamido-diethylphosphonoacetate, is dissolved in 12 ml. of methylene chloride. Triethylamine (0.834 ml.) is added, followed at 0° C. under nitrogen over 4 hours by 0.214 ml. azidoacetyl chloride in 12 ml. of methylene chloride. The mixture is allowed to warm to room temperature, diluted with 180 ml. benzene, washed 3 times with water (at pH 3, 7, 8), dired with MgSO$_3$, filtered and evaporated, affording p-methoxybenzyl dl-3-(1-acetoxyethyl)-7α-azido-3-cephem-4-carboxylate (containing some Δ$^2$ isomer). After chromatography on silica gel using 30 parts of gel per part of product and elution with ethyl acetate-benzene (5:95), the pure product was recovered in 13% yield. Properties: Mass Spectrum M+ at m/e 432 IR (CHCl$_3$) 4.7, 5.55, 5.75, 6.18, 8.04, 9.64μ NMR (CDCl$_3$) τ 8.6 (d, 3, J=8 Hz, CHC$\underline{\text{H}}_3$), 8.0 (s, 3, C$\underline{\text{H}}_3$CO), 6.5 (s, 2, SC$\underline{\text{H}}_2$), 6.2 (s, 3, OC$\underline{\text{H}}_3$), 5.58 (d, 1 J=1.5 Hz, H6 or H7), 5.52 (d, 1, J=1.5 Hz, H7 or H6), 4.8 (s, 2, C$\underline{\text{H}}_2$Ar), 4.04, (q, 1, J=8 Hz, C$\underline{\text{H}}$CH$_3$), 2.8)ABq, 4, Ar$\underline{\text{H}}$).

EXAMPLE 5 p-Methoxybenzyl dl-3-(1-acetoxyethyl)-7α-amino-3-cephem-4-carboxylate p-Methoxbenzyl dl-3-(1-acetoxyethyl)-7α-azido-3-cephem-4-carboxylate (170 mg.) and 170 mg. PtO$_2$ in 25 ml. benzene are treated with hydrogen for 45 minutes at 40 psi. After filtration and evaporation of the solvent, p-methoxybenzyl dl-3-(1-acetoxyethyl)-7α-amino-3-cephem-4-carboxylate is obtained in 97% yield. Properties: IR (CHCl$_3$) 2.91, 3.35, 5.65, 5.78, 6.2, 6.3, 6.75, 6.85, 7.19, 7.30, 7.69, 8.2, 8.5, 9.0, 9.85, 10.55, 10.98, 12.05μ. nmr (CDCl$_3$) μ 8.85 (d, 3, J=8H$_2$, CHC$\underline{\text{H}}_3$), 8.18 br s, 2, N$\underline{\text{H}}_2$), 8.0 (s, 3, C$\underline{\text{H}}_3$CO), 6.6 (s, 2, SC$\underline{\text{H}}_2$), 6.2 (s, 3, OC$\underline{\text{H}}_3$), 5.90 (d, 1, J=1.2Hz, H6 or H7), 5.58 (d, 1, J=1.2 Hz, H7 or H6), 4.82 (s, 2, C$\underline{\text{H}}_2$Ar), 2.85 (ABq, 4, Ar$\underline{\text{H}}$).

The 7α-amino compound prepared in Example 5 is empimerized to the corresponding 7β-amino compound as follows:

Preparation 1 p-Methoxybenzyl dl-3-(1-acetoxyethyl)-7α(p-nitrobenzylideneamino)-3-cephem-4-carboxylate p-Methoxybenzyl dl-3-(1-acetoxyethyl)-7α-amino-3-cephem-4-carboxylate (101 mg.) is treated with 36 mg. p-nitrobenzaldehyde and 0.7 g. of magnesium sulfate in 5 ml. of methylene chloride with stirring for 13 hours. The solution is filtered and evaporated to afford p-methoxybenzyl dl-3-(1-acetoxyethyl)-7α(p-nitrobenzylideneamino)-3-cephem-4-carboxylate in 80% yield. Properties: IR (CHCl$_3$) 3.45, 5.62, 5.78, 5.81, 6.1, 6.23, 6.68, 6.89, 7.3, 7.42, 8.2, 8.5, 8.9, 11.0, 11.65, 12.05μ. NMR (CDCl$_3$) τ 8.56 (d, 3, J=8 Hz, CHC$\underline{\text{H}}_3$), 8.0 (s, 3, C$\underline{\text{H}}_3$CO), 6.5 (s, 2, SC$\underline{\text{H}}_2$), 6.18 (s, 3, OC$\underline{\text{H}}_3$), 5.15 (d, 1, J=1.2 Hz, H6 or H7), 5.07 (d, 1, J=1.2 Hz, H7 or H6), 4.75 (s, 2, ArC$\underline{\text{H}}_2$), 4.0 (q, 1, J=8 Hz, C$\underline{\text{H}}$CH$_3$), 2.82 (ABq, 4, Ar$\underline{\text{H}}$), 2.0 (ABq, 4, Ar$\underline{\text{H}}$), 1.42 (s, 1, C$\underline{\text{H}}$=N).

Preparation 2 p-Methoxybenzyl dl-3-(1-acetoxyethyl)-7β(p-nitrobenzylideneamino)-3-cephem-4-carboxylate p-Methoxybenzyl dl-3-(1-acetoxyethyl)-7α(p-nitrobenzylideneamino)-3-cephem-4-carboxylate (130 mg.) is dissolved in 4 ml. tetrahydrofuran. At −78° C. under nitrogen, 0.163 ml. 2.3 M phenyllithium is added, forming the 7-lithium derivative of p-methoxybenzyl dl-3-(1-acetoxyethyl)-7α(p-nitrobenzylideneamino)-3-cephem-4-carboxylate. Dimethylformamide (5 ml.) is added, and then a mixture of 3 ml. tetrahydrofuran, 0.063 ml. of acetic acid and 0.020 ml. of water. The reaction mixture is warmed to room temperature, diluted with 50 ml. benzene and washed 6 times with water. Wash no. 2 contains pH 2 phosphate buffer, and wash no. 5 pH 8 phosphate buffer. After drying with magnesium sulfate, filtration and evaporation of the solvent, a mixture of p-methoxybenzyl dl-3-(1-acetoxyethyl)-7β(p-nitrobenzylideneamino)-3-cephem-4-carboxylate and p-methoxybenzyl dl-3-(1-acetoxyethyl)-7α(p-nitrobenzylideneamino-3-cephem-4-carboxylate in 85% yield is obtained. The normal isomer shows new bands in the nmr spectrum at τ 4.9 and 4.5 (H6 and H7) and τ 1.2 (C$\underline{\text{H}}$=N).

Preparation 3 p-Methoxybenzyl dl-3-(1-acetoxyethyl)-7β-amino-3-cephem-4-carboxylate

A mixture of p-methoxybenzyl dl-3-(1-acetoxyethyl)-7β(p-nitrobenzylideneamino)-3-cephem-4carboxylate and its 7α-epimer (180 mg.) is treated with 163 mg. of 2,4-dinitrophenyl hydrazine tosylate in 6 ml. of ethanol. The mixture is stirred 30 minutes, filtered, evaporated, treated with pH 8 aqueous buffer and extracted 3 times with ether. The combined ether extracts are dried with MgSO$_4$, filtered and evaporated, leaving a mixture of p-methoxybenzyl dl-3-(1-acetoxyethyl)-7β-amino-3-cephem-4-carboxylate and its 7α-epimer in 97% yield. Properties of 7β-amino derivative: NMR (CDCl$_3$) τ 8.72 (d, 3, J=8 Hz, CHC$\underline{\text{H}}_3$), 8.0 (s, 3, C$\underline{\text{H}}_3$CO), 7.5 (brs, 2, N$\underline{\text{H}}_2$), 6.6 (s, 2, SC$\underline{\text{H}}_2$), 6.3 (s, 3, OC$\underline{\text{H}}_3$), 5.4 (d, 1, J=4.5 Hz, H6 or H7), 5.17 (d, 1, J=4.5 Hz, H7 or H6), 4.8 (s, 2, CH$_2$Ar), 4.0 (q, 1, J=8 Hz, C$\underline{H}$CH$_3$), 2.95 (ABq, 4, Ar$\underline{H}$).

Purification by silica gel column chromatography or silica gel preparative thin layer chromatography affords pure p-methoxybenzyl d, 1-3-(1-acetoxyethyl)-7β-amino-3-cephem-4-carboxylate.

EXAMPLE 6 p-Methoxybenzyl dl-3-(1-acetoxyethyl)-7β(2-thienylacetamido)-3-cephem-4-carboxylate To a solution of 140 mg. of a mixture of p-methoxybenzyl dl-3-(1-acetoxyethyl)-7β-amino-3-cephem-4-carboxylate and its 7α-epimer in 10 ml. of methylene chloride is added successively 0.14 ml. pyridine and a solution of 57 mg. 2-thienylacetyl chloride in 4 ml. of methylene chloride. After 5 minutes stirring at room temperature, the solvent is evaporated and replaced with benzene. The solution is washed with pH 2 phosphate buffer, water, and pH 8 phosphate buffer. After drying with magnesium sulfate, filtration and evaporation of the solvent, p-methoxybenzyl dl-3-(1-acetoxyethyl)-7-(2-thienylacetamido)-3-cephem-4-carboxylate is obtained. It is purified by chromatography on silica gel, which affords p-methoxybenzyl dl-3-(1-acetoxyethyl)-7β(2-thienylacetamido)-3-cephem-4-carboxylate in 17% yield. Properties: Mass Spectrum M+ at m/e 530 IR(CHCl$_3$) 5.60, 5.79, 6.20, 6.64, 8.3, 9.66μ NMR (CDCl$_3$) 8.62 (d, 3, J=7 Hz, CHC$\underline{H}_3$), 8.00 (s, 3, C$\underline{H}_3$CO), 6.63 (s, 2, SC$\underline{H}_2$), 6.20 (s, 3, OC$\underline{H}_3$), 6.18 (s, 2, ArC$\underline{H}_2$CO), 5.12 (d, 1, J=5 Hz, H6), 4.80 (s, 2, ArC$\underline{H}_2$O), 4.26 (dd, 1, J=5 Hz and J=9 Hz, H7), 3.98 (q, 1, J=7 Hz, C$\underline{H}$CH$_3$), 3.55 (d, 1, J=9 Hz, N$\underline{H}$), and 3.2–2.5 (m, 7, Ar$\underline{H}$).

The p-methoxybenzyl dl-3-(1-acetoxyethyl)-7α-(2-thienylacetamido)-3-cephem-4-carboxylate recovered has the following properties: Mass Spectrum M+ at m/e 530 IR (CHCl$_3$) 5.60, 5.78, 5.92, 6.19, 6.62, 8.31μ NMR (CDCl$_3$) 8.63 (d, 3, J=7Hz, CHCH$_3$), 8.03 (s, 3, CH$_3$CO), 6.65(s, 2, SCH$_{-2}$), 6.20(s, 5, OCH$_{-3}$ and ArCH$_{-2}$CO), 5.45 (d, 1, J=2 Hz, H6), 5.10 (dd, 1, J=2 Hz and J=7 Hz, H7), 4.76 (s, 2, ArCH$_2$O), 4.10 (q, 1, J=7 Hz, CHCH$_3$), 3.33 (d, 1, J=7 Hz, N$\underline{H}$), and 3.25–2.5 (m, 7, Ar$\underline{H}$).

EXAMPLE 7

Sodium dl-3-(1-acetoxyethyl)-7β(2-thienylacetamido)-3-cephem-4-carboxylate p-Methoxybenzyl dl-3-(1-acetoxyethyl)—7β(2-thienylacetamido)-3-cephem-4-carboxylate (24 mg.) is dissolved in 0.5 ml. anisole and treated with 2.5 ml. trifluoroacetic acid for 5 minutes at 0° C. The trifluoroacetic acid is pumped off in vacuo at 0° C. and the anisole at ca. 30° C./0.1 mm. More anisole (2 ml.) is added and pumped off. The dl-3-(1-acetoxyethyl)-7β-(2-thienylacetamido)-3-cephem-4-carboxylic acid has the following properties: IR (CHCl$_3$) 5.60, 5.78, 5.94, 6.64, 8.32μ NMR (CDCl$_3$) 8.58 (d, 3, J=7 Hz, CHC$\underline{H}_3$), 7.97 (s, 3, C$\underline{H}_3$CO), 6.60 (s, 2, SC$\underline{H}_2$), 6.12 (s, 2, ArC$\underline{H}_2$), 5.02 (d, 1, J=5 Hz, H6), 4.14 (dd, 1, J=5 Hz and J=9 Hz, H7), 3.85 (q, 1, J=7 Hz, C$\underline{H}$CH$_3$), 3.51 (d, 1, J=9 Hz, N$\underline{H}$), and 3.05–2.45 (m, 3, Ar$\underline{H}$).

The acid is taken up in 5 ml. water containing 3 equivalents of sodium bicarbonate and washed with methylene chloride 3 times. The water layer is acidified to pH 2 with phosphate buffer and extracted with ethyl acetate. The ethyl acetate is then extracted with water containing 3 mg. sodium bicarbonate and the water lyophilized, affording crystalline sodium dl-3-(1-acetoxyethyl)-7β(2-thienylacetamido)-3-cephem-4-carboxylate which has antibacterial activity.

In similar manner but employing other acyloxy compounds such as 1-bromo-3-acetoxy-butan-2-one, 1-chloro-3-propionyloxy-butan-2-one, 1-chloro-3-butyryloxy-butan-2-one, 1-chloro-3-acetoxy-pentan-2-one, 1-bromo-3-propionyloxy-hexan-2-one and the like as starting materials in place of 1-chloro-3-acetoxy-butan-2-one, the corresponding 3-(1-acyloxy)lower alkyl compounds are obtained.

EXAMPLE 8 p-Methoxybenzyl α-(S-phenacylthioimidato)-diethylphosphonoacetate

A mixture of 77 mg. p-methoxybenzyl N-thio-formamido-α-amino-diethylphosphonoacetate, 32 mg. phenacyl chloride, 29 mg. powdered potassium carbonate and 2 ml. acetone is stirred 18 hours at room temperature under nitrogen. The mixture is filtered and evaporated, affording 111 mg. crude p-methoxybenzyl α-(S-phenacylthioimidato)-diethylphosphonoacetate. IR: 5.72μ (ester), 5.93μ (COφ), 6.20, 6.28μ (Ar, C=N). NMR (δ, CDCl$_3$): 1.08, 1.20, 1.32, 3.82, 3.95, 4.08, 4.20, 4.33 [P(OEt)$_2$]; 3.79 (OMe); 4.56 (COC$\underline{H}_2$S), 5.16 (OC$\underline{H}_2$φ); 8.45, 8.51 (SC$\underline{H}$=N); other peaks correct.

When p-chlorophenacyl chloride, p-cyanophenacyl chloride, p-carbomethoxyphenacyl chloride, 4-chloroacetyl-pyridine, 2-chloroacetylfuran and 2-chloroacetyl-5-methyl-furan are used in place of phenacyl chloride in the above-described process, p-methoxybenzyl α-(S-p-chlorophenacyl thioimidato)-diethylphosphonoacetate, p-methoxybenzyl α-(S-p-cyanophenacylthioimidato)-diethylphosphonoacetate, p-Methoxybenzyl α-(S-p-carbomethoxyphenacylthioimidato)-diethylphosphonoacetate, p-methoxybenzyl α-[S-(4-pyridylcarbonylmethyl)thioimidato]-diethylphosphonoacetate, p-methoxybenzyl α-(S-2-furoylmethylthioimidato)-diethylphosphonoacetate and p-methoxybenzyl α-[S-(5-methyl-2-furoylmethyl)thioimidato]-diethylphosphonoacetate are obtained.

Thus, the p-methoxybenzyl α-(S-p-carbomethoxyphenacylthioimidato)-diethylphosphonoacetate so obtained has the following IR and NMR. IR (μ): 5.70 (ester), 5.9 (COAr), 6.20, 6.28 (Ar, C=N). NMR (δ, CDCl$_3$): 3.76 (ArOCH$_3$), 3.94 (COOCH$_3$), 4.53 (COCH$_2$S), 5.12 (OC$\underline{H}_2$Ar), 8.43, 8.50 (SCH=N), other peaks correct.

EXAMPLE 9 p-Methoxybenzyl-5-phenyl-6(H)-1,3-thiazine-4-carboxylate p-Methoxybenzyl α-(S-phenacylthioimidato)-diethylphosphonoacetate, prepared as described in Example 1, is flushed 3 times with tetrahydrofuran, evaporated, dissolved in 1 ml. of 1,2-dimethoxyethane, and treated with 5 mg. of oil-free sodium hydride suspended in 1 ml. of 1,2-dimethoxyethane. After stirring 5 minutes, benzene is added and the solution is washed with water, dried with magnesium sulfate, filtered and evaporated to afford p-methoxybenzyl-5-phenyl-6(H)-1,3-thiazine-4-carboxylate. NMR (δ, CDCl$_3$): 3.40, 3.59, 3.78, 3.97 (SC$\underline{H}_2$); 3.8 (OCH$_3$); 5.0 (OC$\underline{H}_2$φ); 8.3

(SC$\underline{H}$=N); other peaks correct. MS 339, 307, 294, 203, 175, 137, 121.

When p-methoxybenzyl α-(S-p-chlorophenacylthioimidato)-diethylphosphonoacetate, p-methoxybenzyl α-(S-p-cyanophenacylthioimidato)-diethylphosphonoacetate, p-methoxybenzyl α-(S-p-carbomethoxyphenacylthioimidato)-diethylphosphonoacetate, p-methoxybenzyl α-[S-(4-pyridylcarbonylmethyl)thioimidato]-diethylphosphonoacetate, p-methoxybenzyl α-(S-2-furoylmethylthioimidato)-diethylphosphonoacetate and p-methoxybenzyl α-[S-(5-methyl-2-furoylmethyl)thioimidato]-diethylphosphonoacetate are used in place of p-methoxybenzyl-α-(S-phenacylthioimidato)-diethylphosphonoacetate in the above-described process, p-methoxybenzyl-5-p-chlorophenyl-6(H)-1,3-thiazine-4-carboxylate, p-methoxybenzyl-5-p-cyanophenyl-6(H)-1,3-thiazine-4-carboxylate, p-methoxybenzyl-5-p-carbomethoxyphenyl-6(H)-1,3-thiazine-4-carboxylate, p-methoxybenzyl-5-(4-pyridyl)-6(H)-1,3-thiazine-4-carboxylate, p-methoxybenzyl-5-(2-furyl)-6(H)-1,3-thiazine-4-carboxylate and p-methoxybenzyl-5-(5-methyl-2-furyl)-6(H)-1,3-thiazine-4-carboxylate are obtained.

The p-methoxybenzyl-5-p-carbomethoxyphenyl-6(H)-1,3-thiazine-4-carboxylate prepared in this way melts at 144° C. and has the following characteristics. NMR (δ, CDCl$_3$): 3.61 (SCH$_2$), 3.81 (ArOC$\underline{H}_3$), 3.97 (COOCH$_3$), 4.98 (OCH$_2$Ar), 8.43 (SCH=N), other peaks correct. MS: 397, 353, 277, 261, 233, 232, 188, 135, 121.

EXAMPLE 10 p-Methoxybenzyl dl-3-phenyl-7α-azido-3-cephem-4-carboxylate p-Methoxybenzyl-5-phenyl-6(H)-1,3-thiazine-4-carboxylate, prepared as described above form 462 mg. (1.23 mmole) of p-methoxybenzyl N-thioformamido-α-amino-diethylphosphonoacetate, is dissolved in 12 ml. of methylenechloride. Triethylamine (0.834 ml.) is added, followed at 0° C. under nitrogen over 4 hours by 0.214 ml. azidoacetyl chloride in 12 ml. of methylene chloride. The mixture is allowed to warm to room temperature, diluted with 180 ml. benzene, washed 3 times with water (at pH 3, 7, 8) dried with MgSO$_4$, filtered and evaporated, affording 450 mg. of p-methoxybenzyl dl-3-phenyl-7α-azido-3-cephem-4-carboxylate. Chromatography on 20 g. of silica gel and elution with 10:1 chloroform-ethyl acetate gives p-methoxybenzyl dl-3-phenyl-7α-azido-3-cephem-4-carboxylate (containing some Δ$^2$ isomer), 170 mg. IR (μ): 4.72 (azide), 5.59 (lactam), 5.72 (ester). NMR (δ, CDCl$_3$): 4.6d, J=1.5 Hz; 4.7d, J=1.5 Hz (H-6, H-7); other peaks correct. MS: 422, 394, 229, 203, 175.

When p-methoxybenzyl-5-p-chlorophenyl-6(H)-1,3-thiazine-4-carboxylate, p-methoxybenzyl-5-p-cyanophenyl-6(H)-1,3-thiazine-4-carboxylate, p-methoxybenzyl-5-p-carbomethoxyphenyl-6(H)-1,3-thiazine-4-carboxylate, p-methoxybenzyl-5-(4-pyridyl)-6(H)-1,3-thiazine-4-carboxylate, p-methoxybenzyl-5-(2-furyl)-6(H)-1,3-thiazine-4-carboxylate and p-methoxybenzyl-5-(5-methyl-2-furyl)-6(H)-1,3-thiazine-4-carboxylate are used in place of p-methoxybenzyl-5-phenyl-6(H)-1,3-thiazine-4-carboxylate in the above-described process, p-methoxybenzyl dl-3-p-chlorophenyl-7α-azido-3-cephem-4-carboxylate, p-methoxybenzyl dl-3-p-cyanophenyl-7α-azido-3-cephem-4-carboxylate, p-methoxybenzyl dl-3-p-carbomethoxyphenyl-7α-azido-3-cephem-4-carboxylate, p-methoxybenzyl dl-3-(4-pyridyl)-7α-azido-3-cephem-4-carboxylate, p-methoxybenzyl dl-3-(2-furyl)-7α-azido-3-cephem-4-carboxylate and p-methoxy benzyl dl-3-(5-methyl-2-furyl)-7α-azido-3-cephem-4-carboxylate are obtained.

The p-methoxybenzyl dl-3-p-carbomethoxyphenyl-7α-azido-3-cephem-4-carboxylate obtained in this way has the following characteristics. IR (μ): 4.72 (azide), 5.61 (lactam), 5.80 (ester). NMR (δ, CDCl$_3$): 3.61 (CH$_2$S), 4.61d, 4.70d, J=1.5 Hz (H-6, H-7), other peaks correct. MS: 480, 452, 316, 287, 121.

EXAMPLE 11 p-Methoxybenzyl dl-3-phenyl-7α-amino-3-cephem-4-carboxylate p-Methoxybenzyl dl-3-phenyl-7α-azido-3-cephem-4-carboxylate (170 mg.) and 170 mg. PtO$_2$ in 25 ml. benzene are treated with hydrogen for 45 minutes at 40 psi. After filtration and evaporation of the solvent, 101 mg. of p-methozybenzyl dl-3-phenyl-7α-amino-3-cephem-4-carboxylate are obtained. NMR (δ, CDCl$_3$): 4.16d, 4.52d, J=1.5 Hz (H-6, H-7); 2.0 broad (NH$_2$); other peak correct. IR (μ): 5.62 (lactam), 5.72 (ester).

When p-methoxybenzyl dl-3-p-chlorophenyl-7α-azido-3-cephem-4-carboxylate, p-methoxybenzyl dl-3-p-cyanophenyl-7α-azido-3-cephem-4-carboxylate, p-methoxybenzyl dl-3-p-carbomethoxyphenyl-7α-azido-3-cephem-4-carboxylate, p-methoxybenzyl dl-3-(4-pyridyl)-7α-azido-3-cephem-4-carboxylate, p-methoxybenzyl dl-3-(2-furyl)-7α-azido-3-cephem-4-carboxylate and p-methoxybenzyl dl-3-(5-methyl-2-furyl)-7α-azido-3-cephem-4-carboxylate are used in place of p-methoxybenzyl dl-3-phenyl-7α-azido-3-cephem-4-carboxylate in the above-described process, p-methoxybenzyl dl-3-p-chlorophenyl-7α-amino-3-cephem-4-carboxylate, p-methoxybenzyl dl-3-p-cyanophenyl-7α-amino-3-cephem-4-carboxylate, p-methoxybenzyl dl-3-p-carbomethoxyphenyl-7α-amino-3-cephem-4-carboxylate, p-methoxybenzyl dl-3-(4-pyridyl)-7α-amino-3-cephem-4-carboxylate, p-methoxybenzyl dl-3-(2-furyl)-7α-amino-3-cephem-4-carboxylate and p-methoxybenzyl dl-3-(5-methyl-2-furyl)-7α-amino-3-cephem-4-carboxylate are obtained.

The p-methoxybenzyl dl-3-p-carbomethoxyphenyl-7α-amino-3-cephem-4-carboxylate obtained in this way exhibits the following characteristics. IR (μ): 3.0 (NH), 5.62 (lactam), 5.79 (ester). NMR (δ, CDCl$_3$): 4.24d, 4.58d, J=2 Hz (H-6, H-7), 2.3 broad (NH$_2$), other peaks correct. MS: 454, 398, 332, 232, 121.

The 7α-amino compounds are epimerized to the corresponding 7β-amino compounds as follows:

Preparation 1 p-Methoxybenzyl dl-3-phenyl-7α(p-nitrobenzylideneamino)-3-cephem-4-carboxylate p-Methoxybenzyl dl-3-phenyl-7α-amino-3-cephem-4-carboxylate (101 mg.) is treated with 36 mg. p-nitrobenzaldehyde and 0.7 g. of magnesium sulfate in 5 ml. of methylene chloride with stirring for 2 hours. The solution is filtered and evaporated to afford 133 mg. p-methoxybenzyl dl-3-phenyl-7α-(p-nitrobenzylideneamino)-3-cephem-4-carboxylate NMR (CDCl$_3$): C$\underline{H}$=N at 8.55δ.

When p-methoxybenzyl dl-3-p-chlorophenyl-7α-amino-3-cephem-4-carboxylate, p-methoxybenzyl dl-3-p-cyanophenyl-7α-amino-3-cephem-4-carboxylate, p-methoxybenzyl dl-3-p-carbomethoxyphenyl-7α-amino- 3-cephem-4-carboxylate, p-methoxybenzyl dl-3-(4-pyridyl)-7α-amino-3-cephem-4-carboxylate, p-methoxybenzyl dl-3-(2-furyl)-7α-amino-3-cephem-4-carboxylate and p-methoxybenzyl dl-3-(5-methyl-2-furyl)-7α-amino-3-cephem-4-carboxylate are used in place of p-methoxybenzyl dl-3-phenyl-7α-amino-3-cephem-4-carboxylate in the above-described process, p-methoxybenzyl dl-3-p-chlorophenyl-7α(p-nitrobenzylideneamino)-3-cephem-4-carboxylate, p-methoxybenzyl dl-3-p-cyanophenyl-7α-(p-nitrobenzylideneamino)-3-cephem-4-carboxylate, p-methoxybenzyl dl-3-p-carbomethoxyphenyl-7α(p-nitrobenzylideneamino)-3-cephem-4-carboxylate, p-methoxybenzyl dl-3-(4-pyridyl)-7α-(p-nitrobenzylideneamino)-3-cephem-4-carboxylate, p-methoxybenzyl dl-3-(2-furyl)-7α(p-nitrobenzylideneamino)-3-cephem-4-carboxylate and p-methoxybenzyl dl-3-(5-methyl-2-furyl)-7α(p-nitrobenzylideneamino)-3-cepham-4-carboxylate are obtained.

The p-methoxybenzyl dl-3-p-carbomethoxyphenyl-7α-(p-nitrobenzylideneamino)-3-cephem-4-carboxylate prepared by this process has the following characteristics. NMR (δ, CDCl₃): 8.60 (CH=N), other peaks correct.

Preparation 2 p-Methoxybenzyl dl-3-phenyl-7β(p-nitrobenzylideneamino)-3-cephem-4-carboxylate p-Methoxybenzyl dl-3-phenyl-7α(p-nitrobenzylideneamino)-3-cephem-4-carboxylate (130 mg.) is dissolved in 4 ml. tetrahydrofuran. At −78° C. under nitrogen, 0.163 ml. 2.3 M phenyllithium is added, forming the 7-lithium derivative of p-methoxynenzyl dl-3-phenyl-7α(p-nitrobenzylideneamino)-3-cephem-4-carboxylate. Dimethylformamide (5 ml.) is added, and then a mixture of 3 ml. tetrahydrofuran, 0.063 ml. of acetic acid and 0.020 ml. of water. The reaction mixture is warmed to room temperature, diluted with 50 ml. benzene and washed 6 times with water. Wash no. 2 contains pH 2 phosphate buffer, and wash no. 5 pH 8 phosphate buffer. After drying with magnesium sulfate, filtration and evaporation of the solvent, a 2:1 mixture of p-methoxybenzyl dl-3-phenyl-7β(p-nitrobenzylideneamino)-3-cephem-4-carboxylate and p-methoxybenzyl dl-3-phenyl-7α(p-nitrobenzylideneamino)-3-cephem-4-carboxylate are obtained in substantially quantitative yield. The NMR of p-methoxybenzyl dl-3-phenyl-7β(p-nitrobenzylideneamino)-3-cephem-4-carboxylate shows C$\underline{H}$=N at 8.70δ.

When p-methoxybenzyl dl-3p-chlorophenyl-7α(p-nitrobenzylideneamino)-3-cephem-4-carboxylate, p-methoxybenzyl dl-3-p-cyanophenyl-7α(p-nitrobenzylideneamino)-3-cephem-4-carboxylate, p-methoxybenzyl dl-3-p-carbomethoxyphenyl-7α(p-nitrobenzylideneamino)-3-cephem-4-carboxylate, p-methoxybenzyl dl-3-(4-pyridyl)-7α(p-nitrobenzylideneamino)-3-cephem-4-carboxylate, p-methoxybenzyl dl-3-(2-furyl)-7α(p-nitrobenzylideneamino)-3-cephem-4-carboxylate and p-methoxybenzyl dl-3-(5-methyl-2-furyl)-7α(p-nitrobenzylideneamino)-3-cephem-4-carboxylate are used in place of p-methoxybenzyl dl-3-phenyl-7α(p-nitrobenzylideneamino)-3-cephem-4-carboxylate in the above-described process, p-methoxybenzyl dl-3-p-chlorophenyl-7β(p-nitrobenzylideneamino)-3-cephem-4-carboxylate, p-methoxybenzyl dl-3-p-cyanophenyl-7β-(p-nitrobenzylideneamino)-3-cephem-4-carboxylate, p-methoxybenzyl dl-3-p-carbomethoxyphenyl-7β(p-nitrobenzylideneamino)-3-cephem-4-carboxylate, p-methoxybenzyl dl-3-(4-pyridyl)-7β(p-nitrobenzylideneamino)-3-cephem-4-carboxylate, p-methoxybenzyl dl-3-(2-furyl)-7β(p-nitrobenzylideneamino)-3-cephem-4-carboxylate and p-methoxybenzyl dl-3-(5-methyl-2-furyl)-7β(p-nitrobenzylideneamino)-3-cephem-4-carboxylate are obtained.

The p-methoxybenzyl dl-3-p-carbomethoxyphenyl-7β(p-nitrobenzylideneamino)-3-cephem-4-carboxylate prepared in this manner has the following characteristics. NMR (δ, CDCl₃): 8.73 (CH=N), other peaks correct.

Preparation 3 p-Methoxybenzyl dl-3-phenyl-7β-amino-3-cephem-4-carboxylate p-Methoxybenzyl dl-3-phenyl-7β(p-nitrobenzylideneamino)-3-cephem-4-carboxylate (180 mg.) is treated with 163 mg. of 2,4-dinitrophenylhydrazine tosylate in 6 ml. of ethanol. The mixture is stirred 30 minutes, filtered, evaporated, treated with pH 8 aqueous buffer and extracted 3 times with ether. The combined ether extracts are dried with MgSO₄, filtered and evaporated, leaving 140 mg. of p-methoxybenzyl dl-3-phenyl-7β-amino-3-cephem-4-carboxylate. IR (μ): 3.0 (NH₂), 5.64 (lactam), 5.74 (ester).

When p-methoxybenzyl dl-3-p-chlorophenyl-7β(p-nitrobenzylideneamino)-3-cephem-4-carboxylate, p-methoxybenzyl dl-3-p-cyanophenyl-7β(p-nitrobenzylideneamino)-3-cephem-4-carboxylate, p-methoxybenzyl dl-3-p-carbomethoxyphenyl-7β(p-nitrobenzylideneamino)-3-cephem-4-carboxylate, p-methoxybenzyl dl-3-(4-pyridyl)-7β(p-nitrobenzylideneamino)-3-cephem-4-carboxylate, p-methoxybenzyl dl-3-(2-furyl)-7β(p-nitrobenzylideneamino)-3-cephem-4-carboxylate and p-methoxybenzyl dl-3-(5methyl-2-furyl)-7β(p-nitrobenzylideneamino)-3-cephem-4-carboxylate are used in place of p-methoxybenzyl dl-3-phenyl-7β(p-nitrobenzylideneamino)-3-cephem-4-carboxylate in the above-described process, p-methoxybenzyl dl-3p-chlorophenyl-7β-amino-3-cephem-4-carboxylate, p-methoxybenzyl dl-3-p-cyanophenyl-7β-amino-3-cephem-4-carboxylate, p-methoxybenzyl dl-3-p-carbomethoxyphenyl-7β-amino-3-cephem-4-carboxylate, p-methoxybenzyl dl-3-(4-pyridyl)-7β-amino-3-cephem-4-carboxylate, p-methoxybenzyl dl-3-(2-furyl)-7β-amino-3-cephem-4-carboxylate and p-methoxybenzyl dl-3-(5-methyl-2-furyl)-7β-amino-3-cephem-4-carboxylate are obtained.

EXAMPLE 12 p-Methoxybenzyl dl-3-phenyl-7β(2-thienylacetamido)-3-cephem-4-carboxylate

To a solution of 140 mg. p-methoxybenzyl dl-3-phenyl-7β-amino-3-cephem-4-carboxylate in 10 ml. of methylene chloride is added successively 0.14 ml. pyridine and a solution of 57 mg. 2-thienylacetyl chloride in 4 ml. of methylene chloride. After 5 minutes stirring at room temperature, the solvent is evaporated and replaced with benzene. The solution is washed with pH 2 phosphate buffer, water, and pH 8 phosphate buffer. After drying with magnesium sulfate, filtration and evaporation of the solvent, p-methoxybenzyl dl-3-phenyl-7β(2-thienylacetamido)-3-cephem-4-carboxylate is obtained. It is purified by chromatography on 6 g. silica gel, eluting with 10:1 chloroform-ethyl acetate, which affords 27 mg. p-methoxybenzyl dl-3-phenyl-7β(2-thienylacetamido)-3-cephem-4-carboxylate. IR (μ): 3.06 (NH), 5.63 (lactam), 5.77 (ester), 5.97 (amide). NMR (δ, CDCl₃): 3.14, 3.59, 3.82, 4.17 (SCH₂); 3.78 (CH₂CO); 4.9m (OCH₂, 6-H); 5.76, 5.83, 5.90, 5.97 (7α-H). MS: 520, 355, 339, 181.

When p-methoxybenzyl dl-3-p-chlorophenyl-7β-amino-3-cephem-4-carboxylate, p-methoxybenzyl dl-3-p-cyanophenyl-7β-amino-3-cephem-4-carboxylate, p-methoxybenzyl dl-3-p-carbomethoxyphenyl-7β-amino-3-cephem-4-carboxylate, p-methoxybenzyl dl-3-(4-pyridyl)-7β-amino-3-cephem-4-carboxylate, p-methoxybenzyl dl-3-(2-furyl)-7β-amino-3-cephem-4-carboxylate and p-methoxybenzyl dl-3-(5-methyl-2-furyl)-7β-amino-3-cephem-4-carboxylate are used in place of p-methoxybenzyl dl-3-phenyl-7β-amino-3-cephem-4-carboxylate in the above-described process, p-methoxybenzyl dl-3-p-chlorophenyl-7β(2-thienylacetamido)-3-cephem-4-carboxylate, p-methoxybenzyl dl-3-p-cyanophenyl-7β(2-thienylacetamido)-3-cephem-4-carboxylate, p-methoxybenzyl-dl-3-p-carbomethoxyphenyl-7β(2-thienylacetamido)-3-cephem-4-carboxylate, p-methoxybenzyl dl-3-(4-pyridyl)-7β(2-thienylacetamido)-3-cephem-4-carboxylate, p-methoxybenzyl dl-3-(2-furyl)-7β-(2-thienylacetamido)-3-cephem-4-carboxylate and p-methoxybenzyl dl-3-(5-methyl-2-furyl)-7β(2-thienylacetamido)-3-cephem-4-carboxylate are obtained.

The p-methoxybenzyl dl-3-p-carbomethoxyphenyl-7β(2-thienylacetamido)-3-cephem-4-carboxylate so obtained has the following characteristics. IR (μ): 3.0 (NH), 5.61 (lactam), 5.78 (ester), 5.94 (amide). NMR (δ, CDCl₃): 3.58, 3.85m (SCH₂, CH₂CO), 3.79 (ArOCH₃), 3.93 (COOCH₃), 4.91m (OCH₂, 6-H), 5.76, 5.83, 5.91, 5.99 (7α-H), other peaks correct. MS: 578, 457, 397, 261, 232.

EXAMPLE 13

Sodium dl-3-phenyl-7β(2-thienylacetamido)-3-cephem-4-carboxylate p-Methoxybenzyl dl-3-phenyl-7β(2-thienylacetamido)-3-cephem-4-carboxylate (24 mg.) is dissolved in 0.5 ml. anisole and treated with 2.5 ml. trifluoroacetic acid for 5 minutes at 0° C. The trifluoroacetic acid is pumped off in vacuo at 25° C. and the anisole at ca. 30° C/0.1 mm. More anisole (2 ml.) is added and pumped off. The sample is taken up in 5 ml. water containing 3 equivalents of sodium bicarbonate and washed with methylene chloride 3 times. The water layer is acidified to pH 2 with phosphate buffer and extracted with ethyl acetate. The ethyl acetate is then extracted with water containing 3 mg. sodium bicarbonate and the water lyophilized, affording crystalline sodium dl-3-phenyl-7β(2-thienylacetamido)-3-cephem-4-carboxylate (13 mg.) which has antibacterial activity. IR (acid form): 5.60μ (lactam). NMR (Na salt, D₂O,δ): 3.92 (SCH₂), 4.13 (CH₂CO), 4.86 (HDO), 5.38d, 5.90d, J=4.5 Hz (H-6, H-7). High resolution MS of methyl ester (from acid form and CH₂N₂): 414.0713; calc. for C₂₀H₁₈N₂O₄S₂, 414.0707.

When p-methoxybenzyl dl-3-p-chlorophenyl-7β-(2-thienylacetamido)-3-cephem-4-carboxylate, p-methoxybenzyl dl-3-p-cyanophenyl-7β(2-thienylacetamido)-3-cephem-4-carboxylate, p-methoxybenzyl dl-3-p-carbomethoxyphenyl-7β(2-thienylacetamido)-3-cephem-4-carboxylate, p-methoxybenzyl dl-3-(4-pyridyl)-7β(2-thienylacetamido)-3-cephem-4-carboxylate, p-methoxybenzyl dl-3-(2-furyl)-7β-(2-thienylacetamido)-3-cephem-4-carboxylate and p-methoxybenzyl dl-3-(5-methyl-2-furyl)-7β(2-thienylacetamido)-3-cephem-4-carboxylate are used in place of p-methoxybenzyl dl-3-phenyl-7β(2-thienylacetamido)-3-cephem-4-carboxylate in the above-described process, sodium dl-3-p-chlorophenyl-7β(2-thienylacetamido)-3-cephem-4-carboxylate, sodium dl-3-p-cyanophenyl-7β(2-thienylacetamido)-3-cephem-4-carboxylate, sodium dl-3-p-carbomethoxyphenyl-7β(2-thienylacetamido)-3-cephem-4-carboxylate, sodium dl-3-(4-pyridyl)-7β(2-thienylacetamido)-3-cephem-4-carboxylate, sodium dl-3-(2furyl)-7β(2-thienylacetamido)-3-cephem-4-carboxylate and sodium dl-3-(5-methyl-2-furyl)-7β(2-thienylacetamido)-3-cephem-4-carboxylate are obtained.

The sodium dl-3-p-carbomethoxyphenyl-7β(2-thienylacetamido)-3-cephem-4-carboxylate so obtained has the following characteristics. NMR (δ, D₂O): 3.68 (SCH₂), 3.88 (CH₂CO), 4.68 (HDO), 5.16d, 5.67d, J=5 Hz (H-6, H-7), other peaks correct. MS of methyl ester (from sodium dl-3-p-carbomethoxyphenyl-7β(2-thienylacetamido)-3-cephem-4-carboxylate and diazomethane): 472.0714; calc. for C₂₂H₂₀N₂O₆S₂, 472.0763.

EXAMPLE 14 p-Methoxybenzyl α-(S-4-pyridacylthioimidato)-diethylphosphonoacetate

A mixture of 1.75 g N-thioformamido-α-aminodiethylphosphonoacetate, 1.80 g. 4-pyridyl chloromethyl ketone, 2.58 g. K₂CO₃ (pulverized) and 40 ml acetone is stirred for 30 minutes at room temperature under N₂, filtered and evaporated, affording p-Methoxybenzyl α-(S-4-pyridacylthioimidato)-diethylphosphoncacetate. NMR (δ, CDCl₃): 1.2m, 4.0m, P(OEt)₂; 3.80s, OMe; 4.49s, COCH₂S; 5.20s OCH₂φ; 8.44, 8.50, SCH=N; 6.80, 6.95, 7.26, 7.41, C₆H₄; 7.8m, 8.8m, pyridyl.

EXAMPLE 15 p-Methoxybenzyl-5-(4-pyridyl)-6(H)-1,3-thiazine-4-carboxylate p-Methoxybenzyl α-(S-4-pyridacylthioimidato)diethylphosphonoacetate is flushed with benzene, dissolved in 40 ml glyme and treated with 115 mg. oil-free NaH in 25 ml. glyme for 5 minutes. Benzene is added and the solution is washed with water, dried with MgSO₄, filtered and evaporated to yield 2.56 g p-methoxybenzyl-5-(4-pyridyl)-6(H)-1,3-thiazine-4-carboxylate. NMR: (δ, CDCl₃) 3.58s, SCH₂; 4.98s, OCH₂φ; 8.27 s, SCH=N; other peaks correct.

EXAMPLE 16 p-Methoxybenzyl 3-(4-pyridyl)-7α-azido decephalosporanate

To 2.56 g of p-methoxybenzyl-5-(4-pyridyl)-6(H)-1,3-thiazine-4-carboxylate in 100 ml CH₂Cl₂ at 0° is added dropwise a solution of 2.5 ml triethylamine in 100 ml CH₂Cl₂, followed by 1.32 g azidoacetyl chloride in 100 ml CH₂Cl₂, all under nitrogen. After 5 minutes at 25°, the reaction mixture is diluted with benzene, washed with water, dried with MgSO₄, filtered and evaporated, yielding 1.56 g crude p-methoxybenzyl 3-(4-pyridyl)-7α-azido decephalosporanate, which is purified by chromatography on 30 g silica gel, eluting with ethyl acetate. NMR (δ, CDCl₃): 3.62s, SCH₂; 3.80s, OCH₃;

4.66d, 4.70d, J=2 Hz, H-6 and H-7; 5.00s, OCH$_2\phi$; other peaks correct. IR ($\mu$, film): 4.73, azide; 5.61, $\beta$-lactam; 5.78, ester. MS: 423, 395, 230, 175, 194, 121, 104.

EXAMPLE 17 p-Methoxybenzyl 3-(4-pyridyl)-7α-amino decephalosporanate p-Methoxybenzyl 3-(4-pyridyl)-7α-azido decephalosporanate, 117 mg, is hydrogenated in 10 ml benzene 1 hour at 40 psi with 100 mg PtO$_2$, repeating twice more with fresh catalyst. After filtration and evaporation, p-methoxybenzyl 3-(4-pyridyl)-7α-amino decephalosporanate is obtained. IR ($\mu$, film): 3.0, NH$_2$; 5.63, $\beta$-lactam; 5.76, ester. MS: 397, 356, 341, 218, 175, 121.

EXAMPLE 18 p-Methoxybenzyl 3-(4-pyridyl)-7α(p-nitrobenzylideneamino) decephalosporanate p-Methoxybenzyl 3-(4-pyridyl)-7α-amino decephalosporanate, 50 mg, is treated with 99 mg p-nitrobenzaldehyde in 10 ml CH$_2$Cl$_2$ containing 1 g MgSO$_4$ for 2 hours. Filtration and evaporation afford p-methoxybenzyl 3-(4-pyridyl)-7α(p-nitrobenzylideneamino) decephalosporanate.

EXAMPLE 19 p-Methoxybenzyl 3-(4-pyridyl)-7$\beta$(p-nitrobenzylideneamino) decephalosporanate p-Methoxybenzyl 3-(4-pyridyl)-7α(p-nitrobenzylideneamino) decephalosporanate, 120 mg, in 20 ml THF, is added at −78° under N$_2$ to a solution of 130 $\lambda$ 2.3M $\phi$Li in 6 ml THF. DMF, 15 ml, is added, followed by 0.3 ml AcOH in 2 ml THF. The reaction mixture is warmed to 25°, diluted with benzene and washed 6 times with water. Wash No. 5, has pH 8 phosphate buffer. After drying with MgSO$_4$, filtration and evaporation, p-methoxybenzyl 3-(4-pyridyl)-7$\beta$(p-nitrobenzylideneamino) decephalosporanate is obtained in a 1:1 mixture with p-methoxybenzyl 3-(4-pyridyl)-7α(p-nitrobenzylideniamino) decephalosporanate.

EXAMPLE 20 p-Methoxybenzyl 3-(4-pyridyl)-7$\beta$-aminodecephalosporanate p-Methoxybenzyl 3-(4-pyridyl)-7$\beta$(p-nitrobenzylideneamino) decephalosporanate, 120 mg, in ½ ml CH$_2$Cl$_2$, is added to 88 mg 2,4-dinitrophenylhydrazine tosylate in 5 ml EtOH and stirred 30 minutes, filtered and evaporated. The residue is treated with pH 8 aqueous phosphate, extracted 3 × with ether, dried with MgSO$_4$, filtered and evaporated, affording p-methoxybenzyl 3-(4-pyridyl)-7$\beta$-aminodecephalosporanate.

EXAMPLE 21 p-Methoxybenzyl 3-(4-pyridyl)-7$\beta$(2-thienylacetamido) decephalosporanate p-Methoxybenzyl 3-(4-pyridyl)-7$\beta$-aminodecephalosporanate, 52 mg, is treated with 50 ml pyridine and 25 mg 2-thienylacetyl chloride in 10 ml CH$_2$Cl$_2$ 15 minutes, diluted with benzene, washed with water, dried with MgSO$_4$, filtered and evaporated, giving p-methoxybenzyl 3-(4-pyridyl)-7$\beta$-(2-thienylacetamido) decephalosporanate, which is purified by chromatography on silica gel with EtOAc.

EXAMPLE 22

Sodium 3-(4-pyridyl)-7$\beta$(2-thienylacetamido) decephalosporanate

Pure p-methoxybenzyl 3-(4-pyridyl)-7$\beta$(2-thienylacetamido) decephalosporanate, 20 mg, is treated 5 minutes with 0.5 ml anisole and 2.5 ml TFA, pumped at high vacuum, flushed with anisole, taken into 5 ml water with 20 mg NaHCO$_3$, washed with EtOAc, acidified to pH 2 and extracted into EtOAc. Sodium 3-(4-pyridyl)-7$\beta$(2-thienylacetamido) decephalosporanate is extracted back into 2 ml water containing 3 mg NaHCO$_3$ and isolated by lyophilization.

EXAMPLE 23

Thiazole-4-carbonyl chloride

Thiazole-4-carboxylic acid, 0.97 g, is refluxed 1½ hours with 10 ml thionyl chloride, evaporated, flushed with benzene and recrystallized from 50 ml hexane to yield thiazole-4-carbonyl chloride, m.p. 85°. IR ($\mu$, CHCl$_3$): 5.64. NMR ($\delta$, CDCl$_3$): 9.01d, 8.59d, J=2.

EXAMPLE 24

4-Thiazolyl diazomethyl ketone

Thiazole-4-carbonyl chloride, 4.01 g, is treated with 680 ml 0.1 N CH$_2$N$_2$ in ether for 30 minutes at 0° and 30 minutes at 25°. Evaporation of the solvent leaves a yellow solid 4-thiazolyl diazomethylketone which is recrystallized twice from ether, m.p. 82°. NMR ($\delta$, CDCl$_3$): 6.49s, COCHN$_2$; 8.27d, 8.85d, J=2 Hz, H-2 and H-5. IR (CDCl$_3$,$\mu$): 4.72, C=N=N; 6.17, carbonyl.

EXAMPLE 25

4-Thiazolyl chloromethyl ketone

4-Thiazolyl diazomethyl ketone, 0.1 g, is treated in 1 ml ethanol at 0° with HCl gas for a few seconds. Dilution with ether and scratching produces a copious white ppt which is filtered and washed 3× with ether, taken up in water, the pH made to 7 with K$_2$HPO$_4$, and extracted 3× with ether. The ether solution is dried with MgSO$_4$, filtered and evaporated, affording 77 mg 4-thiazolyl chloromethyl ketone. IR (CHCl$_3$) 5.85$\mu$. NMR ($\delta$, CDCl$_3$): 4.95d, J=1, CH$_2$Cl; 8.4m, 8.95m, J=1, H-2 and H-5.

EXAMPLE 26 p-Methoxybenzyl α-(S-2-oxo-2[4-thiazolyl]ethyl thioimidato)-diethylphosphonoacetate A mixture of 2.55 g of N-thioformamido-α-aminodiethylphosphonoacetate, 1.10 g 4-thiazolyl chloromethyl ketone, 2.82 g K$_2$CO$_3$ and 65 ml acetone is stirred 1 hour under N$_2$, filtered, evaporated and chromatographed on 170 g silica gel, eluting with 4:1 ether-acetone, affording 1.24 g pure p-methoxybenzyl α-(S-2-oxo-2[4-thiazolyl]ethyl thioimidato)-diethylphosphonoacetate. IR ($\mu$, CHCl$_3$): 5.74, ester; 5.90, ketone. NMR ($\delta$, CDCl$_3$): 1.3t, 4.1m, J=5, P(OEt)$_2$; 3.81s, OCH$_3$; 4.64s, SCH$_2$; 5.15s, OCH$_2$; 6.78, 6.95, 7.13, 7.27, C$_6$H$_4$; 8.45, 8.51, SCH=N; 8.3m, 8.9m, J=1, thiazole H-2 and H-5.

EXAMPLE 27 p-Methoxybenzyl-5-(4-thiazolyl)-6(H)-1,3-thiazine-4-carboxylate p-Methoxybenzyl α-(S-2-oxo-2[4-thiazolyl]ethyl thioimidato) diethylphosphonoacetate was carried through to p-methoxybenzyl-5-(4-thiazolyl)-6(H)-1,3-thiazine-4-carboxylate without chromatographic purification. It was flushed twice with dry benzene and treated with 57 mg oil-free NaH in 35 ml glyme 5 minutes, diluted with benzene, washed with water, dried with MgSO$_4$, filtered and evaporated to give 1.105 g oil which crystallized. The crystals were washed with benzene-cyclohexane and recrystallized from the same solvent to produce pure p-methoxybenzyl-5-(4-thiazolyl)-6(H)-1,3-thiazine-4carboxylate, m.p. (34°. NMR ($\delta$, CDCl$_3$): 3.84s, OCH$_3$; 5.22s, OCH$_2$; 8.43s, thiazine SCH=N; other peaks correct. MS: 346, 301, 210, 182, 137, 121.

EXAMPLE 28 p-Methoxybenzyl 3-(4-thiazolyl)-7$\alpha$-azido decephalosporanate

To 87 mg p-methoxybenzyl-5-(4-thiazolyl)-6(H)-1,3-thiazine-4-carboxylate in 3 ml CH$_2$CL$_2$ at 0° under N$_2$ is added 87 $\lambda$ triethylamine in 3 ml CH$_2$CL$_2$ and then 33 $\lambda$ azidoacetyl chloride in 3 ml CH$_2$CL$_2$. The reaction is stirred 5 more minutes, diluted with benzene, washed with aqueous pH 3 phosphate, water and pH 8 phosphate, dried with MgSO$_4$, filtered and evaporated to afford 71 mg p-methoxybenzyl 3-(4-thiazolyl)-7$\alpha$-azido decephalosporanate. NMR ($\delta$, CDCl$_3$): 4.68d, 4.72d, J=2 Hz, H-6 and H-7; 5.19s OCH$_2$; other peaks correct. IR ($\mu$, film): 4.72, azide; 5.61, $\beta$-lactam; 5.77, ester. MS: 429, 401, 265, 236.

EXAMPLE 29 p-Methoxybenzyl 3-(4-thiazolyl)-7$\alpha$-amino decephalosporanate p-Methoxybenzyl 3-(4-thiazolyl)-7$\alpha$-azido decephalosporanate, 485 mg, is hydrogenated at 40 psi in 50 ml benzene using 400 mg PtO$_2$ for two hours, then 30 minutes with an additional 400 mg catalyst. The catalyst is filtered through 1:1 supercel-silica gel and washed with ethyl acetate. On evaporation of the filtrate, 254 mg p-methoxybenzyl 3-(4-thiazolyl)-7$\alpha$-amino decephalosporanate is obtained. IR ($\mu$, film): 5.64, $\alpha$-lactam; 5.76, ester. NMR ($\delta$, CDCl$_3$): 2.25, NH$_2$; 4.30d, 4.60d, J=2, H-6 and H-7; other peaks correct. MS: 403, 347, 210, 181, 121.

EXAMPLE 30 p-Methoxybenzyl 3-(4-thiazolyl)-7$\alpha$-(p-nitrobenzylideneamino) decephalosporanate p-Methoxybenzyl 3-(4-thiazolyl)-7$\alpha$-amino decephalosporanate, 380 mg, is treated with 750 mg p-nitrobenzaldehyde in 60 ml CH$_2$Cl$_2$ containing 2 g MgSO$_4$ for 2 hours. Filtration and evaporation afford 420 mg crude crystalline material which gives 220 mg pure p-methoxybenzyl 3-(4-thiazolyl)-7$\alpha$-(p-nitrobenzylideneamino) decephalosporanate after recrystallization from benzene-cyclohexane. IR ($\mu$, Nujol): 5.58, $\beta$-lactam; 5.76, ester. NMR ($\delta$, CDCl$_3$): 5.03d, 5.06d, J=2, H-6 and H-7; 5.26s, OCH$_2$; 8.58 O$_2$NC$_6$H$_4$C$\underline{H}$=N; other peaks correct.

EXAMPLE 31 p-Methoxybenzyl 3-(4-thiazolyl)-7$\beta$(p-nitrobenzylideneamino) decephalosporanate p-Methoxybenzyl 3-(4-thiazolyl)-7$\alpha$(p-nitrobenzylideneamino) decephalosporanate, 40 mg, in 7 ml THF, is added at −78° under N$_2$ to a solution of 10 $\lambda$ Et$_3$N and 33 $\lambda$ 2.3M $\phi$Li in 2 ml THF. DMF, 5 ml, is added, followed by 0.1 ml AcOH in 0.5 ml THF. The reaction mixture is warmed to 25°, diluted with benzene and washed 6× with water; wash No. 2 has pH 3 phosphate and wash No. 5, pH 8. After drying with MgSO$_4$ and evaporation, a 1:1 mixture of p-methoxybenzyl 3-(4-thiazolyl)-7$\beta$(p-nitrobenzylideneamino) decephalosporanate and p-methoxybenzyl 3-(4-thiazolyl)-7$\alpha$(p-nitrobenzylideneamino) decephalosporanate is obtained. IR is like p-methoxybenzyl 3-(4-thiazolyl)-7$\alpha$(p-nitrobenzylideneamino) decephalosporanate. NMR ($\delta$, CDCl$_3$) shows p-methoxybenzyl 3-(4-thiazolyl)-7$\alpha$(p-nitrobenzylideneamino) decephalosporanate anate and p-methoxybenzyl 3-(4-thiazolyl)-7$\beta$(p-nitrobenzylideneamino) decephalosporanate: 5.15d, J=5, 6-H; 5.55q, J=5, 1.5, 7-H; 8.72, O$_2$NC$_6$H$_4$C$\underline{H}$=N; other peaks correct.

EXAMPLE 32 p-Methoxybenzyl 3-(4-thiazolyl)-7$\beta$-amino decephalosporanate 180 mg p-Methoxybenzyl 3-(4-thiazolyl)-7$\beta$(p-nitrobenzylideneamino) decephalosporanate in $\frac{1}{2}$ ml CH$_2$Cl$_2$ is added to 131 mg 2,4-dinitrophenylhydrazine tosylate in 5 ml EtOH and stirred 10 minutes, filtered and evaporated. The residue is treated with pH 8 aqueous phosphate, extracted 3× with ether, dried with MgSO$_4$, filtered and evaporated, leaving p-methoxybenzyl 3-(4-thiazolyl)-7$\beta$-amino decephalosporanate. IR ($\mu$,film): 3.0, NH$_2$; 5.65, $\beta$-lactam; 5.80, ester. NMR ($\delta$, CDCl$_3$): 4.73d, 4.98d, J=5, H-6 and H-7; other peaks correct.

EXAMPLE 33 p-Methoxybenzyl 3-(4-thiazolyl) 7$\beta$(2-thienylacetamido) decephalosporanate p-Methoxybenzyl 3-(4-thiazolyl)-7$\beta$-amino decephalosporanate is treated with 35 $\lambda$ pyridine and 17 mg 2-thienyl acetyl chloride in 5 ml CH$_2$Cl$_2$ for 15 minutes, diluted with benzene, washed with aqueous pH 3 phosphate, water and aqueous pH 8 phosphate, dried with MgSO$_4$, filtered and evaporated, affording 39 mg crude p-methoxybenzyl 3-(4-thiazolyl) 7$\beta$(2-thienylacetamido) decephalosporanate. Pure p-methoxybenzyl 3-(4-thiazdyl) 7$\beta$(2-thienylacetamido) decephalosporanate is obtained by chromatography on 2 g silica gel, eluting with 10:1 CHCl$_3$-EtOAc. IR ($\lambda$, film): 3.0, NH; 5.62, $\beta$-lactam; 5.80, ester; 5.95, amide. NMR ($\delta$, CDCl$_3$): 3.90s, C$\underline{H}_2$CONH; 5.08d, J=5, 6-H; 5.89d of d, J=5, 10, 7-H; 6.38d, J=10, NH; other peaks correct. MS: 527.

EXAMPLE 34

Sodium 3-(4-thiazolyl)-7$\beta$-(2-thienylacetamido) decephalosporanate p-Methoxybenzyl 3-(4-thiazolyl) 7$\beta$(2-thienylacetamido) decephalosporanate in 0.5 ml anisole, is treated with 2.5 ml trifluoroacetic acid at 0° for 4 minutes. The reaction is pumped at high vacuum at 30°, more anisole is added and the pumping repeated. The residue is treated with a few ml water containing 15 mg NaHCO$_3$ and extracted twice with EtOAc. The aqueous portion is then acidified with phosphoric acid to pH 2 and extracted with EtOAc. The latter EtOAc extract is then washed with water containing 4 mg NAHCO$_3$.

The aqueous extract is lyophilized, affording 22 mg sodium 3-(4-thiazolyl)-7β-(2-thienylacetamido) decephalosporanate. MS of methyl ester (from CH$_2$N$_2$): 421.

EXAMPLE 35

Potassium d,1-3-(1-hydroxyethyl)-7β-(2-thienylacetamido)-3-cephem-4-carboxylate

A solution of sodium d,1-3-(1-acetoxyethyl)-7β-(2-thienylacetamido)-3-cephem-4-carboxylate (0.43 g) in aqueous citrus acetyl esterase (13 ml) is placed in a thermostated 30° bath and stirred at that temperature. The pH of the solution is adjusted to 6.7 and is maintained at 6.7 ± 0.1 by addition of 1N sodium hydroxide. When the addition of base becomes very slow, the reaction is stopped. The mixture is brought to room temperature, treated with powdered sodium chloride (4.5 g), and stirred. The resulting thin suspension is overlaid with ethyl acetate (20 ml) and acidified to pH 2.3 with 6N hydrochloric acid. The layers are separated and the aqueous portion is extracted with more ethyl acetate (5 ml.). The combined ethyl acetate solution is layered with water (50 ml) and brought to pH 5.4 with 6N potassium hydroxide and rapid stirring. The aqueous phase is separated, pumped under high vacuum, and lyophilized to afford potassium d,1-3-(1-hydroxyethyl)-7β-(2-thienylacetamido)-3-cephem-4-carboxylate.

EXAMPLE 36 d,1-3-(1-Carbamoyloxyethyl)-7β-(2-thienylacetamido)-3-cephem-4-carboxylic acid

A solution of potassium d,1-3-(1-hydroxyethyl)-7β-(2-thienylacetamido)-3-cephem-4-carboxylate (0.33 g) in 0.05M pH 7 phosphate buffer (10 ml) is mixed with ethyl acetate (10 ml) and cooled in an ice-bath. The pH of the aqueous layer is adjusted to 2.2 with 2.5 N hydrochloric acid. The aqueous layer is separated and extracted with more ethyl acetate (2 × 10 ml). The combined ethyl acetate solution is washed with saturated brine, dried with sodium sulfate, filtered, and evaporated in vacuo to afford d,1-3-(1-hydroxyethyl)-7β-(2-thienylacetamido)-3-cephem-4-carboxylic acid.

The above free acid is dissolved in anhydrous tetrahydrofuran (15 ml) and the solution is cooled to −40° under nitrogen. Chlorosulfonyl isocyanate (0.09 ml) is added. The resulting solution is stirred for 4 hours at −40°, and then treated with 0.1 M pH 7 phosphate buffer (1.5 ml) at that temperature. The tetrahydrofuran is removed in vacuo and the wet residue is treated with 0.1 M pH 7 phosphate buffer (10 ml) and ethyl acetate (10 ml). After stirring for 1 hour at room temperature, the mixture is brought to pH 8 with 2.5 N sodium hydroxide and trisodium phosphate. The organic portion is separated and extracted with 0.1 M pH 7 phosphate buffer (10 ml). The combined aqueous solution is acidified to pH 2.3 with 2.5N hydrochloric acid and extracted with ethyl acetate (2 × 20 ml). The organic extracts are washed with saturated brine, dried over sodium sulfate, filtered, and evaporated in vacuo to yield d,1-3-(1-carbamoyloxyethyl)-7β-(2-thienylacetamido)-3-cephem-4-carboxylic acid.

A portion of the above acid is dissolved in water containing 1.05 equivalents of sodium bicarbonate. The resulting solution is washed once with ethyl acetate, pumped under vacuum to remove dissolved ethyl acetate, and lyophilized to afford sodium d,1-3-(1-carbamoyloxyethyl)-7β-(2-thienylacetamido)-3-cephem-4-carboxylate.

EXAMPLE 37 d,1-3-(1-Acetoxyethyl)-7β-amino-3-cephem-4-carboxylic acid p-Methoxybenzyl d,1-3-(1-acetoxyethyl)-7β-amino-3-cephem-4-carboxylate (0.60 g) is dissolved in anisole (2 ml) and the solution is cooled to 0°. Ice-cold trifluoroacetic acid (10 ml) is then added and the resulting solution is kept at 0° for 10 minutes. The trifluoroacetic acid is removed in vacuo at 0° followed by warming to 30° in vacuo to remove excess anisole. The resulting gum is partitioned between water and ethyl acetate. The aqueous portion is separated and brought to pH 4 to precipitate d,1-3-(1-acetoxyethyl)-7β-amino-3-cephem-4-carboxylic acid.

EXAMPLE 38 d,1-7β-Amino-3-ethyl-3-cephem-4-carboxylic acid

A solution of d,1-3-(1-acetoxyethyl)-7β-amino-3-cephem-4-carboxylic acid (0.23 g) in water (3.5 ml) containing sodium bicarbonate (0.14 g) is hydrogenated at 40 psi over 5% palladium on barium sulfate (0.88 g). The catalyst is removed by suction filtration and washed with 5% aqueous sodium bicarbonate (0.5 ml). The combined filtrate and wash is diluted with 6N hydrochloric acid (2 ml), treated with charcoal (0.3 g), and filtered. The clear filtrate is cooled in an ice-bath and brought to pH 3.8 with 2N sodium hydroxide to precipitate d,1-7β-amino-3-ethyl-3-cephem-4-carboxylic acid.

EXAMPLE 39 d,1-7β-(D-2-t-butoxycarboxamido-2-phenylacetamido)-3-ethyl-3-cephem-4-carboxylic acid A solution of D-2-t-butoxycarboxamido-2-phenylacetic acid (126 mg) and triethylamine (70 μl.) in anhydrous tetrahydrofuran (2 ml) is stirred at −10° under a nitrogen atmosphere. Isobutyl chloroformate (65 μl) is added, and the mixture is stirred at −10° for 15 minutes. During this period, a solution of triethylammonium d,1-7β-amino-3-ethyl-3-cephem-4-carboxylate is prepared by added triethylamine (70 μl) to an ice-cold, stirring suspension of d,1-7β-amino-3-ethyl-3-cephem-4-carboxylic acid (114 mg) in 50% aqueous tetrahydrofuran (2 ml). The cold salt solution is added to the mixed anhydride solution with stirring. The resulting mixture is stirred at 0° for 1 hour and at room temperature for 1 hour. Evaporation of the tetrahydrofuran in vacuo leaves a residue which is partitioned between water (3 ml) and ethyl acetate (1 ml). The aqueous portion is separated, cooled in an ice-bath, layered with ethyl acetate (3 ml), and acidified to pH 3 with 2.5 N hydrochloric acid. The layers are separated and the aqueous portion extracted with more ethyl acetate (2 ml). The combined ethyl acetate extracts are washed with water and brine, dried over magnesium sulfate, filtered and evaporated in vacuo to yield d,1-7β-(D-2-t-butoxycarboxamido-2-phenylacetamido)-3-ethyl-3-cephem-4-carboxylic acid.

EXAMPLE 40 d,1-7β-(D-2-Amino-2-phenylacetamido)-3-ethyl-3-cephem-4-carboxylic acid d,1-7β-(D-2-t-butoxycarboxamido-2-phenylacetamido)-3-ethyl-3-cephem-4-carboxylic acid (100 mg) is dissolved in ice-cold trifluoroacetic acid (1 ml). The solution is stirred at 5° until gas evolution ceases, and then poured into anhydrous ether to precipitate the trifluoroacetate salt of the title compound. The salt is dissolved in water (0.5 ml) and treated with a 25% solution of Amberlite LA-1 (acetate form) in methyl isobutyl ketone (1 ml). After stirring and cooling for 1 hour, the precipitate of d,1-7β-(D-2-amino-2-phenylacetamido)-3-ethyl-3-cephem-4-carboxylic acid is collected, washed with water and methyl isobutyl ketone, and dried in vacuo.

EXAMPLE 41 p-Methoxybenzyl d,1-3-(1-acetoxyethyl)-7β-(p-nitrobenzylideneamino)-7-methylthio-3-cephem-4-carboxylate A solution of p-methoxybenzyl d,1-3-(1-acetoxyethyl)-7α-(p-nitrobenzylideneamino)-3-cephem-4-carboxylate (1.08 g) in anhydrous tetrahydrofuran (30 ml) is stirred and cooled to −78° under a nitrogen atmosphere. Phenyllithium (0.87 ml of a 2.3 M solution in 7:3 benzene-ether) is added to give the deep blue anion. After stirring one more minute, anhydrous dimethylformamide (35 ml) is added dropwise over 4 minutes. Freshly prepared methylsulfenyl chloride (0.17 g) in tetrahydrofuran (5 ml) is then added dropwise over one minute. The reaction mixture is stirred for 2 more minutes at −78°, and then it is allowed to warm to room temperature over 15 minutes. Benzene (500 ml) is added and the resulting orange solution is washed with water (6 × 300 ml) and saturated brine. The second wash is acidified with 1 M pH 3 phosphate buffer and the fifth is basified with 1 M dipotassium hydrogen phosphate. The benzene solution is dried with magnesium sulfate, filtered, and evaporated in vacuo to an oil. Chromatography of this material on silica gel (35 g), using 5% ethyl acetate in chloroform as eluting solvent, affords p-methoxybenzyl d,1-3-(1-acetoxyethyl)-7β-(p-nitrobenzylideneamino)-7-methylthio-3-cephem-4-carboxylate.

EXAMPLE 42 p-Methoxybenzyl d,1-3-(1-acetoxyethyl)-7β-amino-7-methylthio-3-cephem-4-carboxylate A mixture of 2,4-dinitrophenylhydrazine (0.23 g) and p-toluenesulfonic acid monohydrate (0.22 g) in tetrahydrofuran (5 ml) is stirred at room temperature for 30 minutes. A solution of p-methoxybenzyl d,1-3-(1-acetoxyethyl)-7β-(p-nitrobenzylideneamino)-7-methylthio-3-cephem-4- carboxylate (0.67 g) in tetrahydrofuran (5 ml) is added and the resulting mixture is stirred for 60 minutes at room temperature. The mixture is filtered and the filtrate is concentrated in vacuo. The residue is diluted with 1 M dipotassium hydrogen phosphate (2.5 ml) and water (17.5 ml) and extracted with ether (3 × 20 ml). The combined extracts are washed with water and saturated brine, dried over magnesium sulfate, filtered, and evaporated in vacuo to yield p-methoxybenzyl d,1-3-(1-acetoxyethyl)-7β-amino-7-methylthio-3-cephem-4-carboxylate as an orange oil.

EXAMPLE 43 p-Methoxybenzyl d,1-3-(1-acetoxyethyl)-7β-(2-thienylacetamido)-7-methylthio-3-cephem-4-carboxylate Pyridine (0.45 ml) and 2-thienylacetyl chloride (0.18 g) are added to an ice-cold, stirring solution of p-methoxybenzyl d,1-3-(1-acetoxyethyl)-7β-amino-7-methylthio-3-cephem-4-carboxylate (0.51 g) in dry methylene chloride (15 ml). The resulting solution is stirred in the cold for 15 minutes, and then it is diluted with benzene (100 ml). The benzene solution is washed with two portions of pH 2 phosphate buffer, water, pH 9 phosphate buffer, water, and saturated brine, dried with magnesium sulfate, filtered, and evaporated in vacuo to an oil. The crude product is purified by column chromatography on silica gel (20 g). Elution with 20% ethyl acetate in benzene affords p-methoxybenzyl d,1-3-(1-acetoxyethyl)-7β-(2-thienylacetamido)-7-methylthio-3-cephem-4-carboxylate.

EXAMPLE 44 p-Methoxybenzyl d,1-3-(1-acetoxyethyl)-7β-(2-thienylacetamido)-7-methoxy-3-cephem-4-carboxylate p-Methoxybenzyl d,1-3-(1-acetoxyethyl)-7β-(2-thienylacetamido)-7-methylthio-3-cephem-4-carboxylate (0.52 g) is dissolved in methanol (10 ml) and the solution is stirred at room temperature. Thallium (III) nitrate trihydrate (0.40 g) in methanol (5 ml) is added, and the resulting mixture is stirred for 10 minutes at room temperature. Sodium bicarbonate (0.23 g) is then added and stirring continued for 2 more minutes. The mixture is filtered and the filtrate is concentrated under reduced pressure. The residue is taken up in methylene chloride and filtered to remove salts. The filtrate is washed with water, dilute aqueous dipotassium hydrogen phosphate, water, and brine, dried with magnesium sulfate, filtered, and evaporated in vacuo to an oil. The crude product is chromatographed on silica gel (15 g) using 20% ethylacetate in benzene as eluting solvent to afford p-methoxybenzyl d,1-3-(1-acetoxyethyl)-7β-(2-thienylacetamido)-7-methoxy-3-cephem-4-carboxylate.

EXAMPLE 45 d,1-3-(1-Acetoxyethyl)-7β-(2-thienylacetamido)-7-methoxy-3-cephem-4-carboxylic acid Ice-cold trifluoroacetic acid (6.5 ml) is added to a cold mixture of p-methoxybenzyl d,1-3-(1-acetoxyethyl)-7β-(2-thienylacetamido)-7-methoxy-3-cephem-4-carboxylate (292 mg) and anisole (1.3 ml). The mixture is swirled to make homogeneous, and then kept at 0° for 5 minutes. The trifluoroacetic acid is removed in vacuo at 0° and the residue allowed to warm to room temperature in vacuo. The resulting gum is taken up in water (40 ml) containing sodium bicarbonate (0.44g) and extracted with methylene chloride (2 × 20 ml). The aqueous phase is acidified to pH 2.6 with 1 M pH 2 phosphate buffer and extracted with ethyl acetate (3 × 20 ml). The combined ethyl acetate extracts are dried over magnesium sulfate, filtered, and evaporated in vacuo to yield d,1-3-(1-acetoxyethyl)-7β-(2-thienylacetamido)-7-methoxy-3-cephem-4-carboxylic acid.

The above free acid is stirred with sodium bicarbonate (48 mg) in water (15 ml) for 10 minutes. After washing with ethyl acetate (2 × 5 ml), the aqueous solution is lyophilized to afford sodium d,1-3-(1-acetoxyethyl)-7β-(2-thienylacetamido)-7-methoxy-3-cephem-4-carboxylate as an off-white powder.

EXAMPLE 46

Potassium d,1-3-(1-hydroxyethyl)-7β-(2-thienylacetamido)-7-methoxy-3-cephem-4-carboxylate To a 1-dram vial equipped with a magnetic stirrer is added sodium d,1-3-(1-acetoxyethyl)-7β-(2-thienylacetamido)-7-methoxy-3-cephem-4-carboxylate (95 mg.) and citrus acetyl esterase (2.6 ml.). The resulting solution is placed in a thermostated 30° bath and stirred at that temperature. The pH of the reaction mixture is maintained at 6.7 ± 0.1 by addition of 1N sodium hydroxide. After 15 hours, the rate of base addition is very slow and the reaction is stopped. The reaction mixture is brought to room temperature, treated with powdered sodium chloride (900 Mg.), and stirred. The resulting suspension is overlaid with ethylacetate (4 ml.) and, with vigorous stirring, the pH is adjusted to 2.1 with 6N hydrochloric acid. The layers are separated and the aqueous portion extracted with more ethyl acetate (2 × 1 ml.). The combined ethyl acetate solution is back-washed with water (2 × 2 ml.), then layered with water (12.5 ml.) and stirred vigorously while 6N potassium hydroxide is added to pH 5.4. The aqueous phase is separated, pumped under vacuum to remove dissolved ethyl acetate, and lyophilized to yield potassium d,1-3-(1-hydroxyethyl)-7β-(2-thienylacetamido)-7-methoxy-3-cephem-4-carboxylate.

EXAMPLE 47 d,1-3-(1-carbamoyloxyethyl)-7β-(2-thienylacetamido)-7-methoxy-3-cephem-4-carboxylic acid Potassium d,1-3-(1-hydroxyethyl)-7β-(2-thienylacetamido)-7-methoxy-3-cephem-4-carboxylate (61 mg.) is dissolved in 0.05M pH7 phosphate buffer (2 ml.) and the solution is layered with ethyl acetate (12 ml.). The mixture is stirred in an ice-bath and the pH is adjusted to 2.2 with 2.5N hydrochloric acid. The organic layer is separated and the organic portion extracted with ethyl acetate (2 × 2 ml.). The combined ethyl acetate solution is washed with saturated brine, dried over sodium sulfate, filtered, and evaporated in vacuo to yield d,1-3-(1-hydroxyethyl)-7β-(2-thienylacetamide)-7-methoxy-3-cephem-4-carboxylic acid.

The above free acid is dissolved in anhydrous tetrahydrofuran (3 ml.) and the solution is cooled to −40° under nitrogen. Chlorosulfonyl isocyanate (15μl.) is added and the resulting solution is stirred at −40° for 4 hours. The reaction mixture is treated with 0.1M pH7 phosphate buffer (0.3 ml.) at −40°, and the tetrahydrofuran is removed in vacuo. The wet residue is treated with 0.1M pH7 phosphate buffer (2 ml.) and ethyl acetate (2 ml.). The mixture is stirred rapidly for 1 hour at room temperature. The pH of the mixture is brought to 8 by addition of 5% aqueous trisodium phosphate and 2.5N sodium hydroxide. The organic layer is separated and washed with 0.1M pH7 phosphate (2 ml.). The combined aqueous layers are acidified to pH 2.2 with 2.5N hydrochloric acid and extracted with ethyl acetate (2 × 5 ml.). The combined ethyl acetate extracts are washed with saturated brine, dried over sodium sulfate, filtered, and evaporated in vacuo to give d,1-3-(1-carbamoyloxyethyl)-7β-(2-thienylacetamido)-7-methoxy-3-cephem-4-carboxylic acid.

A portion of the above free acid is stirred with water containing 1.05 equivalents of sodium bicarbonate. The resulting solution is washed with ethyl acetate and lyophilized, affording sodium d,1-3-(1-carbamoyloxyethyl)-7β-(2-thienylacetamido)-7-methoxy-3-cephem-4-carboxylate.

EXAMPLE 48 d,1-7β-(2-thienylacetamido)-3-(1-pyridiniumethyl)-3 cephem-4-carboxylate

A solution of d,1-7β-(2-thienylacetamido)-3-(1-acetoxyethyl)-3-cephem-4-carboxylic acid (0.20 g.), potassium thiocyanate (0.10 g.), and pyridine (0.10 ml.) in water (0.50 ml.) is acidified to pH 6.5 with 85% phosphoric acid and stirred in a thermostated 60° bath for 4 hours. After cooling to room temperature, the solution is extracted with 25% Amberlite LA-1 (acetate form) in methyl isobutyl ketone (6×ml.). The aqueous solution on cooling overnight at 5° yields a precipitate of d,1-7β-(2-thienylacetamido)-3-(1-pyridinium ethyl)-3-cephem-4-carboxylate.

EXAMPLE 49 d,1-7β-amino-3-[1-(1-methyl-1,2,3,4-tetrazol-5-yl)thioethyl]-3-cephem-4-carboxylic acid A saturated solution of sodium bicarbonate is added with stirring to a mixture of d,1-7β-amino-3-(1-acetoxyethyl)-3-cephem-4-carboxylic acid (286 mg.) in water (2 ml.) and acetone (1 ml.) until the pH is 7.9. The resulting solution is placed in a thermostated 60° bath and treated with a solution of 1-methyl-1,2,3,4-tetrazole-5-thiol (174 mg.) in acetone (1 ml.). The mixture is heated in the bath at 60° for 3 hours and then cooled in an ice-bath, whereupon the pH is adjusted to 4 with 6N hydrochloric acid. The cold mixture is stirred for 30 minutes, and the precipitate is collected, washed with acetone, and dried in vacuo to afford d,1-7β-amino-3-[1-(1-methyl-1,2,3,4-tetrazol-5-yl)thioethyl]-3-cephem-4-carboxylic acid.

EXAMPLE 50 d,1-7β-(D-2-formyloxy-2-phenylacetamido)-3-[1-(1-methyl-1,2,3,4-tetrazol-5-yl)thioethyl]-3-cephem-4-carboxylic acid A solution of D-2-formyloxy-2-phenylacetyl chloride (199 mg.) in acetone (2 ml.) is added to an ice-cold solution of d,1-7β-amino-3-[1-(1-methyl-1,2,3,4-tetrazol-5-yl)thioethyl]-3-cephem-4-carboxylic acid (171 mg.) and sodium bicarbonate (250 mg.) in water (5 ml.) and acetone (5 ml.). The resulting mixture is stirred in the cold for 1 hour and for 1 more hour at room temperature. The acetone is evaporated in vacuo. The aqueous residue is diluted with water (5 ml.), layered with ethyl acetate (10 ml.), cooled in an ice-bath, and acidified with stirring to pH2 with 6N hydrochloric acid. The ethyl acetate portion is separated, washed with water, dried over magnesium sulfate, filtered, and evaporated in vacuo to give crude d,1-7β-(D-2-formyloxy-2-phenylacetamido)-3-[1-(1-methyl-1,2,3,4-tetrazol-5-yl)thioethyl]-3-cephem-4-carboxylic acid.

EXAMPLE 51 d,1-7β-(D-2-hydroxy-2-phenylacetamido)-3-[-1-(1-methyl-1,2,3,4-tetrazol-5yl)thioethyl]-3-cephem-4-carboxylic acid A solution of d,1-7β-(D-2-formyloxy-2-phenylacetamido)-3-[1-(1-methyl-1,2,3,4-tetrazol-5-yl)thioethyl]-3-cephem-4-carboxylic acid (246 mg.) in water (3ml.) containing sodium bicarbonate (250 mg.) is stirred at room temperature for 3 hours. The solution is diluted with water (5 ml.), layered with ethylacetate (5 ml.), cooled in an ice-bath, stirred, and acidified to pH2 with 6N hydrochloric acid. The ethyl acetate phase is separated, washed with water, dried over magnesium sulfate, filtered, and evaporated in vacuo to afford d,1-7β-(D-2-hydroxy-2-phenylacetamido)-3-[1-(1-methyl-1,2,3,4-tetrazol-5yl)thioethyl]-3-cephem-4-carboxylic acid.

A sample of the free acid in ethanol is treated with 1 equivalent of 1N methanolic sodium acetate. Stirring and cooling gives a percipitate of sodium d,1-7β-(D-2-hydroxy-2-phenylacetamido)-3-[1-(1-methyl-1,2,3,4-tetrazol-5-yl)thioethyl]-3-cephem-4-carboxylate.

EXAMPLE 52 d,1-7β-[1-(1H)-tetrazolylacetamido]-3-(1-acetoxyethyl-3-cephem-4-carboxylic acid To an ice-cold solution of d,1-7β-amino-3-(1-acetoxyethyl)-3-cephem-4-carboxylic acid (0.29 g.) and sodium bicarbonate (0.27 g.) in water (5 ml.) and acetone (3.5 ml.) is added dropwise with stirring a solution of 1-(1H)-tetrazolylacetyl chloride (0.22 g.) in acetone (1.8 ml.). The reaction mixture is stirred for 1 hour at 5° and for 2 more hours at room temperature. The pH is maintained at 7.5 ± 0.5 by addition of saturated sodium bicarbonate solution. The acetone is evaporated in vacuo. The aqueous residue is acidified to pH 1 with 6N hydrochloric acid and extracted with ethyl acetate. The ethyl acetate portion is evaporated in vacuo, leaving d,1-7β-[1-(1H)-tetrazolylacetamido]-3-(1-acetoxyethyl)-3-cephem-4-carboxylic acid.

EXAMPLE 53 d,1-7β-[1-(1H)-tetrazolylacetamido]-3-[1-(5-methyl-1,3,4-thiadiazol-2-yl)thioethyl]-3-cephem-4-carboxylic acid A solution of d,1-7β-[1-(1H)-tetrazolylacelamido]-3-(1-acetoxyethyl-3-cephem-4-carboxylic acid (100 mg.), sodium bicarbonate (20 mg.), and 2-mercapto-5-methyl-1,3,4-thiadiazole (38 mg.) in pH6.4 phosphate buffer (2 ml.) is stirred for 3 hours at 60°. After cooling to room temperature, the reaction mixture is acidified to pH2 with 6N hydrochloric acid and extracted with ethyl acetate. The organic layer is separated, washed with brine, dried with magnesium sulfate, filtered, and evaporated in vacuo to afford d,1-7β-[1-(1H)-tetrazolylacetamido]-3-[1-(5-methyl-1,3,4-thiadiazol-2-yl)thioethyl]-3-cephem-4-carboxylic acid.

A sample of the above free acid (45 mg.) in water (0.1 ml.) containing sodium bicarbonate (9 mg.) is diluted with ethanol (0.5 ml.). The solution is left in a refrigerator overnight, and the precipitate of sodium d,1-7β-[1-(1H)-tetrazolylacetamido]-3-[1-(5-methyl-1,3,4-thiadiazol-2-yl)thioethyl]-3-cephem-4-carboxylate is collected and dried in vacuo.

In similar manner following the procedures of the above examples but using heterocyclic substituted compounds of the general formula

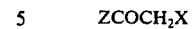

where X is a halogen such as bromine or chlorine and Z is a heterocyclic group such as furyl, thienyl, thiazolyl, thiadiazolyl, pyridyl, pyrazolyl, tetrazolyl and the like or a substituted heterocyclic group having one or more alkyl, alkoxy, halo, cyano, carboalkoxy or other substituents in place of the phenacyl chloride, the corresponding 3-heterocyclic cephem compound is obtained.

The new dl cephem compounds prepared as described above can be resolved by methods known in the art to obtain the enantiomers. Thus, for example, the esters can be cleaved to produce the free acids which can be reacted with optically active bases, the resulting diastereomeric salts can be separated by fractional crystallization, and the optically active salts can be converted to other salts such as amine and metal salts which are suitable for therapeutic use.

The dl cephem compounds and the active enantiomers are valuable antimicrobial substances which are active against various gram-positive and gram-negative pathogens such as *Bacillus subtilis, Salmonella schottmuelleri* and *Proteus vulgaris*. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicilins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules, suppositories, syrups, elixers and the like which can be prepared in accordance with procedures well known in this art.

In the foregoing examples, the carboxy group is blocked or protected by forming a p-methoxybenzyl ester which is later removed to obtain the free acid. In place of the p-methoxybenzyl ester, other esters, for example lower alkyl esters such as methyl, ethyl or tertiary butyl, substituted alkyl esters such as phthalimidomethyl, succinimidoethyl alkloxyalkyl esters such as methoxymethyl, phenacyl, substituted phenacyl esters such as p-bromo phenacyl, an aryloxy alkyl ester such as p-methoxyphenoxymethyl, an aralkyloxy alkyl ester such as benzyloxymethy, a substituted benzyl ester such as p-nitrobenzyl, 3,5-di-nitrobenzyl, 2,4,6-trimethylbenzyl, or 3,5-dichloro-4-hydroxybenzyl, benzhydryl or a substituted benzhydryl ester such as p-methoxybenzhydryl or β-substituted ethyl esters such as $CH_2CCl_3$ and $CH_2CH_2SCH_3$ and the like can be used. Thus, examples of other suitable starting materials that might be mentioned are the trichloroethyl, benzhydryl, t-butyl, methyl, phenacyl, p-bromophenacyl, methoxymethyl, and p-methoxyphenoxyethyl esters of α-thioformamidodiethylphosphonoacetic acid.

The p-methoxybenzyl α-thioformamido-diethylphosphonoacetate used as the starting material in the foregoing examples can be prepared as follows:

To a solution of benzylamine in absolute alcohol is added a molar equivalent of 37% aqueous formaldehyde and the reaction mixture is allowed to stir at room temperature for 2 hours. The 1,3,5-tribenzyl-sym-hexahydrotriazine found in the reaction is recovered by extraction with petroleum ether which, after evaporation, yields a product melting at 48°–50° C. The latter product is heated with about 3 molar equivalents of diethyl phosphite at 100° C. for 6 hours, and the resulting reaction product is chromatographed on silica gel using 3% methanol in methylene chloride as the eluting solvent. Evaporation of the solvent affords diethyl N-benzyl-aminomethylphosphonate as a pale yellow mobile liquid. Hydrogenation of this product in absolute alcohol containing a small amount of HCl in the presence of palladium on carbon catalyst affords diethyl aminomethylphosphonate hydrochloride which is recovered by evaporating the filtered hydrogenation mixture. Reaction of this product in chloroform with ammonia and evaporation of the resulting filtered solution yields diethyl aminomethylphosphonate. Benzaldehyde is added to this product in an ice bath to produce diethyl N-benzylidene-aminomethylphosphonate which is recoverd by diluting the reaction mixture with absolute alcohol and evaporating the filtered solution. The product is further purified by solution in dry benzene and evaporation of the solvent to afford the product as a pale yellow oil. To a solution of the diethyl N-benzylidene-aminomethylphosphonate in dry tetrahydrofuran is then added phenyllithium solution followed by the slow addition of p-methoxybenzyl chloroformate. After about 20 minutes, the solvent is removed under reduced pressure and the oily residue is partitioned between ethyl ether and pH 3 phosphate buffer. Evaporation of the ethyl ether affords p-methoxybenzyl N-benzylidene-α-amino-diethylphosphonoacetate which is purified by chromatography over silica gel using 1:3 ethyl acetate:ethyl ether as the eluting solvent. The product so obtained is reacted with p-toluenesulfonic acid in ethyl ether solution and cyclohexane is added to the reaction mixture. The solvent layer is decanted and the resulting oily layer is again washed with 2:1 ethyl ether-cyclohexane. Solution of the oily residue in aqueous dipotassium phosphate to pH about 7 and extraction of the solution with methylene chloride affords a solvent solution of the product which is evaporated to produce p-methyoxybenzyl α-amino-diethylphosphonoacetate. Reaction of this product with ethyl thioformate in the presence of liquid hydrogen sulfide at low temperatures produces crude p-methoxybenzyl α-thioformamido-diethylphosphonoacetate. The latter product is purified over silica gel using ethyl acetate to elute the product.

As will be apparent to those skilled in this art, other esters of the starting material can be prepared in the same way using the appropriate ester of chloroformic acid in this synthesis.

Pharmaceutically acceptable salts which may be formed using procedures well known to the art from the compounds of the invention include (a) inorganic base salts such as alkali metal, e.g. sodium and potassium, alkaline earth e.g. calcium, and organic base salts, e.g. procaine and dibenzylethylene diamine salts and (b) acid addition salts, e.g. with hydrochloric, hydrobromic, sulphuric, nitric, phosphoric, toluene-p-sulphonic and methanesulphonic acids. In addition to salts, the novel cephalosporins of the invention may be administered in the form of esters, including those discussed above. Examples of esters that might be mentioned are esters of alcohols, phenols, mercaptans, and thiophenols of the general formula—$COXR_4$ wherein $R_4$ represents the radical of an alcohol or a thiol such as methyl, ethyl, tertiary butyl, a substituted alkyl such as phthalimidomethyl, succinimidomethyl, phenacyl, a substituted phenacyl for example p-bromophenacyl, a β-substituted ethyl group such as 2,2,2-trichloroethyl, 2-(p-methylphenyl)ethyl, 2-(p-methylphenyl)sulfonylethyl, 2-methylaminoethyl, 2-chloro(or bromo)ethyl, benzyl, a substituted benzyl group such as p-nitrobenzyl, p-methoxybenzyl, 3,5-dinitrobenzyl, 2,4,6-trimethylbenzyl, 3,5-dichloro-4-hydroxybenzyl, and the like, a benzhydryl or substituted benzhydryl group such as p-methoxybenzhydryl, an acyloxy alkyl group such as acetoxymethyl, pivaloyloxymethyl, an alkoxy group such as methoxymethyl, or a monocyclic aryl group for example phenyl or substituted phenyl such as p-nitrophenyl or 3,5-dinitrophenyl of interest are the alkenyl esters (e.g. 3-buten-1-yl). These esters are readily prepared in accordance with processes well known in this art.

The novel cephalosporins are valuable antibiotics active against various gram-positive and gram-negative bacteria and, accordingly, find utility in human and veterinary medicine. The compounds of this invention can therefore be used an antibacterial drugs for treating infections caused by gram-positive or gram-negative bacteria, for example against *Staphylococcus aureus* (penicillin resistant), *Escherichia coli, Klebsiella pneumoniae, Salmonella typhosa, Pseudomonas* and *Bacterium proteus.* The antibacterial cephalosporins of the invention may further be utilized as additives to animal feedingstuffs, for preserving foodstuffs and as disinfectants. For example, they may be employed in aqueous compositions in compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose aluminum stearate gel or hydrogenated edible fats; emulsifying agents, for example lecithin, sorbitan monooleate or acacia; non-aqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight. The preferred daily dosage for the compounds of the invention range from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10 – 60%. The composition will generally contain from about 15 mg. to about 1500 mg. by weight of the active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution. Typical formulations of specific products are described below.

One such unit dosage form consists in mixing 120 mg. of sodium-3-(1-acetoxyethyl)-7B(2-thienylacetamido)-3-cephem-4-carboxylate with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| Sodium dl-3-phenyl-7B(2-thienylacetamido)-3-cephem-4-carbotylate | 125. mg. |
| Cornstarch, U.S.P. | 6. mg. |
| Dicalcium Phosphate | 192. mg. |
| Lactose, U.S.P. | 190. mg. |

The active ingredient is blended with the dicalcium phosphate, lactose and about half of the cornstarch. The mixture is then granulated with a 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

PARENTERAL SOLUTION

| Ampoule: | |
|---|---|
| Sodium-3-(4-pyridyl)-7B(2-thienylacetamido)-decephalosporanate | 500 mg. |
| Ampoule: | |
| Diluent: Sterile Water for Injection | 2 cc. |

By substituting an equivalent amount of sodium 3-(4-thiazolyl)-7B(2-thienylacetamido)decephalosporanate for the 500 mg. of material utilized in the foregoing example there is also obtained a formulation suitable for parenteral administration.

OPTHALMIC SOLUTION

| 3-(1-carbamoyloxylthyl)-7B-(2-thienylacetamido)-3-cephem-4-carboxylic acid | 100 mg. |
|---|---|
| Hydroxypropylmethyl Cellulose | 5 mg. |
| Sterile Water | to 1 ml. |

OTIC SOLUTION

| 7B(D-2-amino-2-phenylacetamido-3 ethyl-3-cephem-4-carboxylic acid | 100 mg. |
|---|---|
| Benzalkonium Chloride | 0.1 mg. |
| Sterile Water | to 1 ml. |

TOPICAL OINTMENT

| 3-(1-carbamoyloxyethyl)-7B-(2-thienylacetamido)-7-methoxy-3-cephem-4-carboxylic acid | 100 mg. |
|---|---|
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example with other antibacterial agents such as lincomycin, a penicllin, streptomycin, novobiocin, gentamicin, neomycin, colistin and kanamycin, or with other therapeutic agents such as probenecid.

What is claimed is:

1. A compound having the structure:

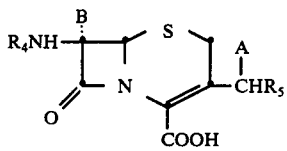

wherein: $R_4$ is an acyl radical selected from the group consisting of:

wherein: R" is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)-5-methyl-4-isoxazolyl, D-4-amino-4-carboxybutyl, D-4-N-benzoylamino-4-carboxy-n-butyl, p-aminobenzyl,

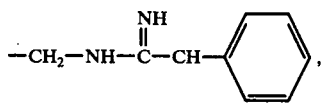

o-aminobenzyl, m-aminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-napthylmethyl, 3-isothiazolylmethyl, 4-isothiazolylmethyl, 5-isothia-zolylmethyl, 4-pyridiylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)-methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl) methyl, 2- or 3-(5-methoxythienyl)methyl, 2- or 3-(4-chlorothienyl)-methyl, 2- or 3-(5-sulfothienyl)methyl, 2- or 3-(5-carboxythienyl)methyl, 3-(1,2,5-thiadiazolyl) methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, or tetrazolylmethyl; or the radical $R_4$ is represented by:

$$-\overset{O}{\underset{\|}{C}}(CH_2)_nZR''$$

wherein $n$ is 0–4, Z represents oxygen or sulfur, and R" is defined above; or the radical $R_4$ is represented by:

$$-\overset{O}{\underset{\|}{C}}-\underset{R'''}{\overset{|}{C}}HR''$$

wherein R" is defined as above and R'" is a radical selected from the group consisting of: amino, hydroxy, azido, carbamoyl, guanidino, halo, sulfamino, tetrazolyl, sulfo, and carboxy; B is hydrogen or methoxyl; $R^5$ is a $C_1$–$C_3$ straight or branched chain alkyl; A is a heterocyclylthio radical selected from the group consisting of: isoxazolylthio, pyrolidenylthio, 1,3,4-thiadiazolylthio, 1-oxidopyridylthio, furazanylthio, tetrazolylthio, thienylthio, thiazolylthio, furylthio, pyranylthio, pyrrolylthio, imidazolylthio, pyrazolylthio, pyridylthio, pyrazinylthio, pyrimidinylthio, pyridazinylthio, isothiazolylthio, and 1-methyl-1,2,3,4-tetrazolyl-5-thio; and the non-toxic pharmaceutically acceptable salts and esters thereof.

2. A compound according to claim 1 wherein B is hydrogen.

3. 7β-[1-(1H)-tetrazolylacetamido]-3-[1-(5-methyl-1,3,4-thiadiazolyl-2-yl)thioethyl]-3-cephem-4-carboxylic acid, and the pharmaceutically aceptable salts and esters thereof.

* * * * *